(12) United States Patent
Mizutani et al.

(10) Patent No.: US 8,168,054 B2
(45) Date of Patent: May 1, 2012

(54) GAS SENSING ELEMENT WITH INCREASED RESPONSE

(75) Inventors: Keigo Mizutani, Okazaki (JP); Shinya Teranishi, Kariya (JP); Katsuhide Akimoto, Nishio (JP); Shoichiro Emmei, Nagoya (JP)

(73) Assignees: Nippon Soken, Inc., Nishio (JP); Denso Corporation, Kariya (JP)

( * ) Notice: Subject to any disclaimer, the term of this patent is extended or adjusted under 35 U.S.C. 154(b) by 419 days.

(21) Appl. No.: 12/405,635

(22) Filed: Mar. 17, 2009

(65) Prior Publication Data
US 2009/0229978 A1    Sep. 17, 2009

(30) Foreign Application Priority Data

Mar. 17, 2008  (JP) .................................. 2008-067501

(51) Int. Cl.
*G01N 27/41* (2006.01)
(52) U.S. Cl. ....................... 204/429; 204/428
(58) Field of Classification Search ............ 204/421–429
See application file for complete search history.

(56) References Cited

U.S. PATENT DOCUMENTS

| | | | |
|---|---|---|---|
| 4,902,400 A * | 2/1990 | Usami et al. .................. | 204/426 |
| 5,672,811 A | 9/1997 | Kato et al. | |
| 5,866,799 A | 2/1999 | Kato et al. | |
| 5,939,615 A | 8/1999 | Kato et al. | |
| 6,076,393 A | 6/2000 | Kato et al. | |
| 6,196,053 B1 * | 3/2001 | Kato et al. .................... | 73/31.05 |
| 6,383,354 B1 * | 5/2002 | Kurokawa et al. ............ | 204/425 |

FOREIGN PATENT DOCUMENTS

| | | |
|---|---|---|
| JP | 08-271476 | 10/1996 |
| JP | 11-201940 | 7/1999 |

OTHER PUBLICATIONS

Japanese Office Action dated Nov. 17, 2009, issued in corresponding Japanese Application No. 2008-067501, with English translation.

* cited by examiner

*Primary Examiner* — Kaj K Olsen
*Assistant Examiner* — Kourtney R Salzman
(74) *Attorney, Agent, or Firm* — Nixon & Vanderhye PC

(57) ABSTRACT

A gas sensing element is disclosed as having a measuring gas chamber to which measuring gases are admitted, a diffusion resistance portion for introducing measuring gases to the measuring gas chamber under diffusion resistance, a sensor cell for detecting a specified gas concentration of measuring gases, and an oxygen pump cell for adjusting an oxygen concentration in the measuring gases. The sensor cell includes a measuring electrode, placed facing the measuring gas chamber, and a reference electrode formed in pair with the measuring electrode. The oxygen pump cell includes an inner pump electrode placed facing the measuring gas chamber, and an outer pump electrode formed in pair with the inner pump electrode. The diffusion resistance portion is placed in an area inside of external end walls of the inner pump electrode to be exposed to the measuring gas chamber.

19 Claims, 26 Drawing Sheets

GAS SENSING ELEMENT WITH INCREASED RESPONSE

CROSS REFERENCE TO RELATED APPLICATIONS

This application is based on Japanese Patent Application No. 2008-67501 filed on Mar. 17, 2008, the content of which is hereby incorporated by reference.

BACKGROUND OF THE INVENTION

1. Technical Field of the Invention

The present invention relates to gas sensing elements and, more particularly, to a gas sensing element having a sensor cell for detecting a specified gas concentration in measuring gases admitted to a measuring gas chamber and an oxygen pump cell for adjusting an oxygen concentration in the measuring gas chamber.

2. Description of the Related Art

Attempts have been made to install gas sensors on exhaust systems of, for instance, automotive vehicles for measuring a specified gas concentration in measuring gases such as a NOx concentration in exhaust gases.

The gas sensors usually include gas sensing elements, one of which is disclosed, for instance, in FIG. 26 (which is extracted from Patent Publication: Japanese Patent Application No. H8-271476). The gas sensing element 9 includes a sensor cell 93 for detecting a specified gas concentration in measuring gases, and an oxygen pump cell 92 for adjusting an oxygen concentration in a measuring gas chamber 91.

Due to an adverse affect caused by oxygen contained in measuring gases, it is likely that a difficulty arises in accurately measuring a concentration of specified gas to be measured in nature. In view of such a difficulty, the gas sensing element 9 allows the oxygen pump cell 92 to adjust the oxygen concentration in the measuring gas chamber 91 to suppress such an adverse affect.

As shown in FIG. 26, more particularly, the gas sensing element 9 includes a plurality of solid electrolyte bodies 95 between which a first inner empty space 911 and a second inner empty space 912 are defined. The first inner empty space 911 admits measuring gases through a first diffusion rate-controlling passage 961 formed in one of the solid electrolyte bodies 95. The second inner empty space 912 communicates with the first inner empty space 911 via a second diffusion rate-controlling passage 962.

The sensor cell 93 includes a measuring electrode 931 exposed to the second inner empty space 912. Likewise, the oxygen pump cell 92 includes an inner pump electrode 921 exposed to the first inner empty space 911. In addition, the sensor cell 93 also includes a reference electrode 932, acting in pair with the measuring electrode 931, which is exposed to a reference gas chamber 913. Moreover, an outer pump electrode 922, acting in pair with the inner pump electrode 921, is located on the gas sensing element 9 at an outer area thereof.

Further, the measuring electrode 931 of the sensor cell 93 is located in the second inner empty space 912 and the inner pump electrode 921 of the oxygen pump cell 92 is located in the first inner empty space 911. Furthermore, the reference electrode 932, acting in pair with the measuring electrode 931, is located in the reference gas chamber 913. Moreover, the outer pump electrode 922, acting in pair with the inner pump electrode 921, is located on the gas sensing element 9 at the outer area thereof.

Furthermore, the first inner empty space 911 encompasses an inner monitor electrode 941 of an oxygen monitor cell 94 for detecting the oxygen concentration in the first inner empty space 911. The oxygen monitor cell 94 is comprised of the inner monitor electrode 941 and the reference electrode 932, between which an electromotive force occurs to allow the oxygen concentration to be detected in the first inner empty space 911.

With the gas sensing element 9 of such a structure, measuring gases are admitted to the first inner empty space 911 via the first diffusion rate-controlling passage 961. When this takes place, the oxygen pump cell 92 pumps out oxygen in measuring gases to the outside, causing a reduction in oxygen concentration in measuring gases. Measuring gases, lowered in oxygen concentration, are admitted to the second inner empty space 912 via the second diffusion rate-controlling passage 962.

The sensor cell 93, having the measuring electrode 931 located in the second inner empty space 912, measures a specified gas concentration in measuring gases. When this takes place, the oxygen concentration in measuring gases is adequately lowered with a resultant decrease in adverse affect caused by the oxygen concentration, thereby minimizing an error in measuring the specified gas concentration.

Meanwhile, the oxygen monitor cell 94 monitors the oxygen concentration in measuring gases admitted to the first inner empty space 911. The oxygen pump cell 92 provides an output varying depending on a resulting measured result of the oxygen concentration for thereby varying a capacity of pumping oxygen. This allows the oxygen concentration in measuring gases to be maintained at a fixed level in the first inner empty space 911.

However, the gas sensing element 9 of such a related art encounters various issues as described below.

That is, the measuring gas chamber 91 of the gas sensing element 9 is separated into the first inner empty space 911 and the second inner empty space 912 and juxtaposed along a longitudinal direction Y of the gas sensing element 9. The first diffusion rate-controlling passage 961, acting to admit measuring gases, is formed in the solid electrolyte body 95 at an end portion of the first inner empty space 911 in opposition to the second inner empty space 912 so as to extend in a stack direction Z. Thus, the measuring gases, admitted through the first diffusion rate-controlling passage 961, need to flow in a long distance to reach the measuring electrode 931 of the sensor cell 93 in the second inner empty space 912. As a consequence, the gas sensing element 9 has a risk of a drop in response.

SUMMARY OF THE INVENTION

The present invention has been completed with a view to addressing such an issue and has an object to provide a gas sensing element having increased measuring precision with excellent response.

To achieve such an object, there is provided a gas sensing element comprising: first and second solid electrolyte bodies extending in a longitudinal direction and stacked on each other in a stack direction with a space therebetween for defining a measuring gas chamber; a diffusion resistance portion placed adjacent to the measuring gas chamber to admit measuring gases thereto under given diffusion resistance; a sensor cell mounted on the first solid electrolyte body for detecting a specified gas concentration of measuring gases admitted to the measuring gas chamber; and an oxygen pump cell mounted on the second solid electrolyte body for adjusting an oxygen concentration in the measuring gas chamber. The sensor cell includes a measuring electrode, formed on a surface of the first solid electrolyte body facing the measuring gas chamber, and a reference electrode formed on the other surface of the first solid electrolyte body in pair with the measuring electrode. The oxygen pump cell includes an inner pump electrode, formed on a surface of the second solid electrolyte body facing the measuring gas chamber, and an outer pump electrode formed on the other surface of the second solid electrolyte body in pair with the inner pump electrode. The diffusion resistance portion extends from the measuring gas chamber on a plane perpendicular to the stack direction at a position inward of external end walls of the inner pump electrode. The measuring electrode is located in the measuring gas chamber at an area inside of the inner pump electrode.

The gas sensing element of the present invention has advantageous effects as described below.

The diffusion resistance portion is formed in the measuring gas chamber on the plane perpendicular to the stack direction of the first and second solid electrolyte bodies. This enables a reduction in distance between an external end wall of the diffusion resistance portion, i.e., an inlet of measuring gases, and the measuring electrode, thereby allowing the gas sensing element to have increased response in operation.

Further, the measuring electrode is placed in the measuring gas chamber at the area inward of the external end walls of the inner pump electrode. This enables the oxygen pump to adjust the oxygen concentration in measuring gases before the measuring gases reach the measuring electrode. Accordingly, the gas sensing element can have increased measuring precision.

As set forth above, the present invention makes it possible to provide a gas sensing element that has increased measuring precision with excellent response in operation.

With the gas sensing element of the present invention, examples of the specified gas may include, for instance, NOx (Nitrogen Oxides), CO (Carbon Monoxide) and HC (Hydrocarbon), etc.

Further, the gas sensing element of the present invention can be applied to an exhaust system of an internal combustion engine such as, for instance, an automotive engine or the like.

With the gas sensing element according to the present invention, the diffusion resistance portion and the inner pump electrodes may be preferably placed adjacent to each other in the stack direction.

With such a structure, measuring gases tend to be adequately brought into contact with the inner pump electrode before passing through the diffusion resistance portion to be admitted to the measuring gas chamber. During such movement of measuring gases, the oxygen pump cell can adequately pump oxygen, thereby making it possible to properly adjust the oxygen concentration in measuring gases.

With the gas sensing element according to the present invention, further, the diffusion resistance portion may be preferably formed along a direction perpendicular to the longitudinal direction.

With such a structure, particularly, a distance between the external end walls of the diffusion resistance portion, i.e., the inlet of measuring gases, and the measuring electrode can be formed in the shortest length, enabling the gas sensing element to have a further increase in response.

With the gas sensing element according to the present invention, furthermore, the inner pump electrode and the measuring electrode may be preferably formed in areas juxtaposed along the longitudinal direction thereof, and the measuring electrode is spaced from an inner end wall of the inner pump electrode.

With such a structure, the oxygen pump cell can properly adjust the oxygen concentration in measuring gases, which in turn are supplied to the measuring electrode. This results in a capability of measuring the specified gas concentration at increased precision.

According to the present invention, the gas sensing element may further comprise an oxygen monitor cell mounted on the first solid electrolyte body for measuring an oxygen concentration in the measuring gas chamber. The oxygen monitor cell may preferably include an inner monitor electrode, formed on the surface of the first solid electrolyte body facing the measuring gas chamber, and an outer monitor electrode formed on the other surface of the first solid electrolyte body in pair with the inner monitor electrode. The monitor electrode may be preferably located in an area inside the inner pump electrode.

With such a structure, the oxygen concentration in the measuring gas chamber can be accurately determined to be used for the oxygen pump cell to perform feedback control and the sensor cell to correct a measured value. This enables the gas sensing element to have increased measuring precision. In addition, the inner monitor electrode is disposed in the area inside of the external end walls of the inner pump electrode. This enables the oxygen pump cell to adjust the oxygen concentration, after which the oxygen monitor cell can accurately measure the adjusted oxygen concentration in the measuring gases.

In particular, when attempting to decrease the distance between an external end wall of the diffusion resistance portion and the measuring electrode for providing increased response, there is a risk of the occurrence of a decrease in width of the inner pump electrode with a difficulty of adequately ensuring oxygen pumping capacity. Therefore, the provision of the oxygen monitor cell minimizes a fluctuation in oxygen concentration in the measuring gas chamber or allows the measured value to be corrected, thereby ensuring precision of detecting the specified gas concentration.

With the gas sensing element, further, the inner monitor electrode may be preferably spaced from an inner end wall of the inner pump electrode.

With such a structure, measuring gases, with the oxygen concentration being properly adjusted with the oxygen pump cell, can be supplied to the inner monitor electrode, thereby making it possible to provide improved precision of measuring the oxygen concentration.

According to the present invention, the gas sensing element may further comprise a power supply for applying a voltage to the oxygen pump cell, and a pump circuit for regulating the voltage applied to the oxygen pump cell based on a detection signal on an oxygen concentration detected with the oxygen monitor cell.

With such a structure, the oxygen concentration in the measuring gas chamber can be easily kept at a fixed level. In particular, when attempting to decrease the distance between an external end wall of the diffusion resistance portion and the measuring electrode for providing increased response, there is a risk of the occurrence of a decrease in width of the inner pump electrode with a difficulty of adequately ensuring oxygen pumping capacity. Therefore, compelling the oxygen monitor cell to monitor the oxygen concentration in the measuring gas chamber while permitting a resulting detected signal to be fed back to the oxygen pump cell, thereby making it possible to easily adjust the oxygen concentration.

According to the present invention, the gas sensing element may further comprise a first power supply for applying a given voltage across the measuring electrode and the reference electrode to allow an electric current to flow therebetween depending on the specified gas concentration and the oxygen concentration of the measuring gases, and a second power supply for applying a given voltage across the inner monitor electrode and the outer monitor electrode to allow an electric current to flow therebetween depending on the oxygen concentration of the measuring gases. The specified gas concentration is detected based on a difference between a current value flowing through the sensor cell and a current value flowing through the oxygen monitor cell.

Such a structure enables the sensor cell to correct a measured value of the specified gas concentration, thereby making it possible to obtain an accurate measured value.

With the gas sensing element, furthermore, the diffusion resistance portion may preferably have at least a part composed of a porous body.

Such a structure enables the diffusion resistance portion to easily adjust diffusion resistance.

With the gas sensing element, moreover, the diffusion resistance portion may be preferably located between the measuring electrode and the inner pump electrode to act as diffusion resistance for the measuring gases.

With such a structure, the oxygen pump cell can properly adjust the oxygen concentration to allow a resultant specified gas to be supplied to the measuring electrode, thereby making it possible to measure the specified gas concentration with increased precision.

With the gas sensing element, further, an external end wall of the diffusion resistance portion and the measuring electrode may be preferably spaced by the shortest distance of 1 to 3 mm.

With such a structure, it becomes possible to provide a gas sensing element that can have adequately improved response in operation with properly increased measuring precision.

If the shortest distance is less than 1 mm, then, an oxygen concentration adjustment achieved with the oxygen pump cell becomes inadequate in operation, resulting in a risk of a drop in measuring precision. On the contrary, the shortest distance exceeds 3 mm, then, there is a risk of a difficulty occurring in adequately improving response.

According to the present invention, there is provided a gas sensing element comprising: first and second solid electrolyte bodies extending in a longitudinal direction and stacked on each other in a stack direction; a measuring gas chamber formed between first and second solid electrolyte bodies; a reference gas chamber defined on one surface of the first solid electrolyte body; and a sensor cell mounted on the first solid electrolyte body for detecting a specified gas concentration of measuring gases admitted to the measuring gas chamber; an oxygen pump cell mounted on the second solid electrolyte body for adjusting an oxygen concentration in the measuring gas chamber. The sensor cell includes a measuring electrode, formed on the other surface of the first solid electrolyte body facing the measuring gas chamber, and a reference electrode formed on the one surface of the first solid electrolyte body in pair with the measuring electrode to be exposed to the reference gas chamber. The oxygen pump cell includes an inner pump electrode disposed in the measuring gas chamber, and an outer pump electrode formed on the other surface of the second solid electrolyte body in pair with the inner pump electrode. A diffusion resistance portion, placed between the first and second solid electrolyte bodies on the same plane as the inner pump electrode and exposed to the measuring gas chamber, extends in parallel to the inner pump electrode in close proximity thereto for admitting measuring gases to the measuring gas chamber under given diffusion resistance. The measuring electrode is located in the measuring gas chamber at an area inside of the inner pump electrode.

BRIEF DESCRIPTION OF THE DRAWINGS

These and other features and advantages of the present invention will become more apparent in light of the following description, as illustrated in the accompanying drawings, in which.

DETAILED DESCRIPTION OF PREFERRED EMBODIMENTS

Now, gas sensing elements of various embodiments according to the present invention will be described below in detail with reference to the accompanying drawings. However, the present invention is construed not to be limited to such embodiments described below and technical concepts of the present invention may be implemented in combination with other known technologies or other technologies having functions equivalent to such known technologies.

In the following description, it is to be understood that such terms as "inner", "outer", "external", "inward", "inside", "perpendicular", "longitudinal", "stack" and the like are words of convenience and are not to be construed as limiting terms.

First Embodiment

Now, a gas sensing element of a first embodiment according to the present invention will be described below in detail with reference to FIGS. 1 to 4 of the accompanying drawings.

Figure 1:
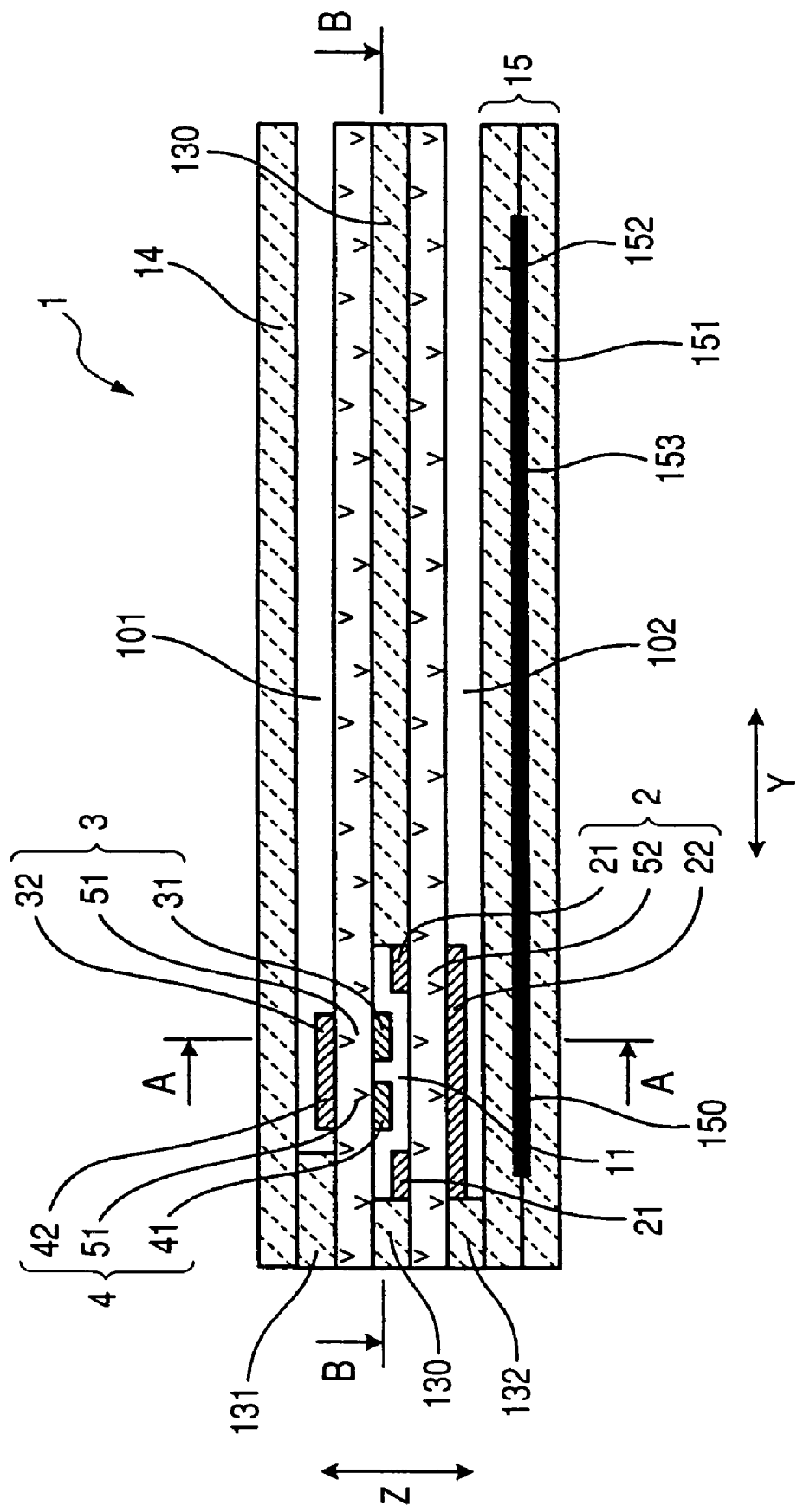
FIG. 1 is a view showing a gas sensing element of a first embodiment according to the present invention in cross section taken on a plane parallel to a longitudinal direction Y and a stack direction Z.
Figure 2:
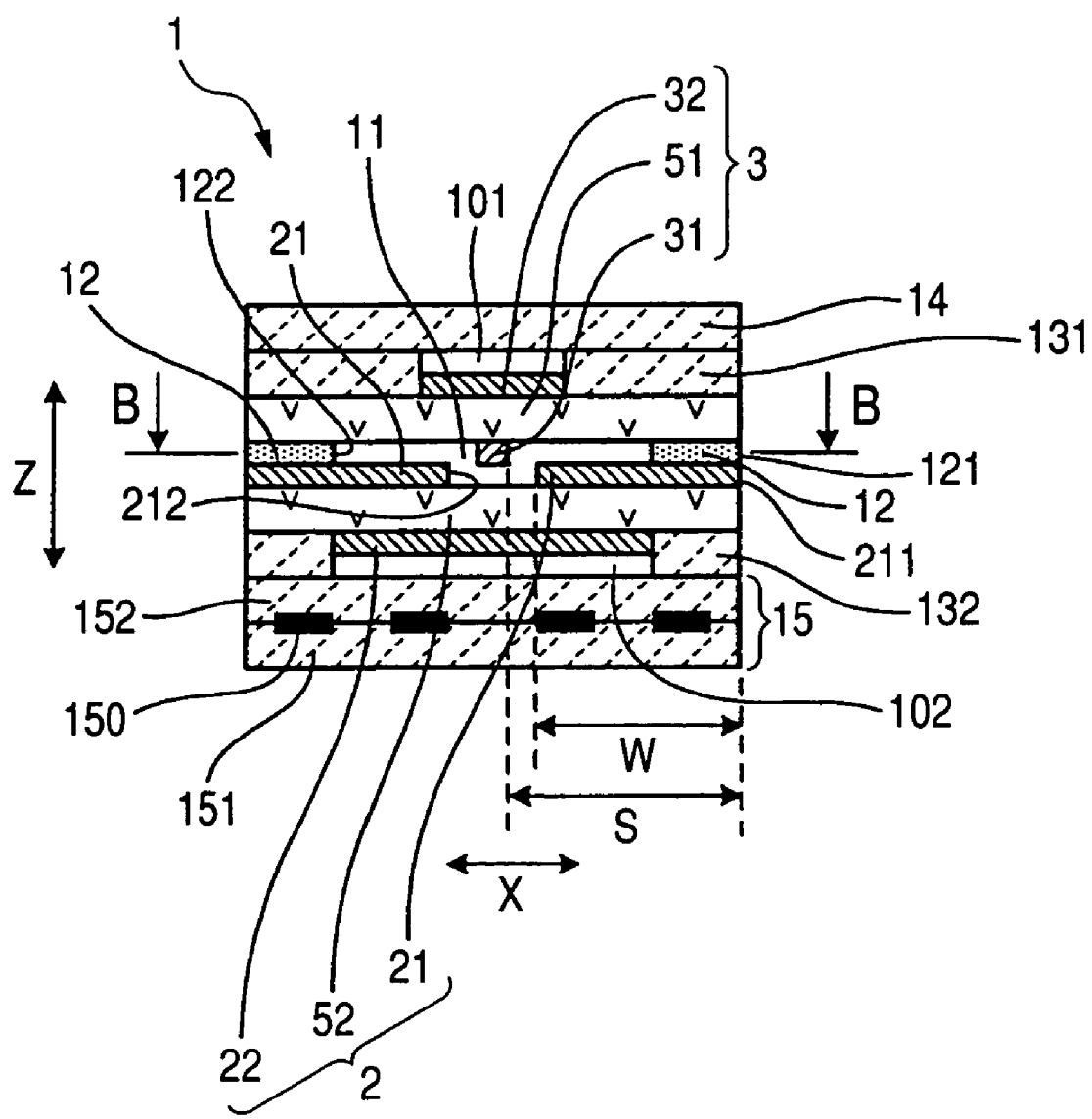
FIG. 2 is a cross sectional view of the gas sensing element taken on line A-A of FIG. 1.

As shown in FIGS. 1 and 2, the gas sensing element 1 includes first and second solid electrolyte bodies 51 and 52, each having oxygen ion conductivity, a measuring gas chamber 11 defined between the first and second electrolyte bodies 51 and 52 for introducing measuring gases, and diffusion resistance portions 12 sandwiched between the first and second electrolyte bodies 51 and 52 for admitting measuring gases to the measuring gas chamber 11 under given diffusion resistance.

Further, the gas sensing element 1 includes a sensor cell 3 for detecting a concentration of specified gas contained in measuring gases admitted to the measuring gas chamber 11, an oxygen pump cell 2 for adjusting a concentration of oxygen prevailing in the measuring gas chamber 11, and an oxygen monitor cell 4 for measuring an oxygen concentration in the measuring gas chamber 11.

The sensor cell 3 includes the first solid electrolyte body 51, a measuring electrode 31 formed on the first electrolyte body 51 at one surface thereof facing the measuring gas chamber 11, and a reference electrode 32 formed on the first electrolyte body 51 at the other surface thereof in pair with the measuring electrode 31.

The oxygen pump cell 2 includes the second solid electrolyte body 52, an inner pump electrodes 21 formed on the second electrolyte body 52 at one surface thereof facing the measuring gas chamber 11, and an outer pump electrode 22 formed on the second electrolyte body 52 at the other surface thereof in pair with the inner pump electrodes 21.

The oxygen monitor cell 4 includes the first solid electrolyte body 51, an inner monitor electrode 41 formed on the first electrolyte body 51 at one surface thereof facing the measuring gas chamber 11, and an outer monitor electrode 42 formed on the first electrolyte body 51 at the other surface thereof in pair with the inner monitor electrode 41.

The diffusion resistance portions 12 is formed in a direction perpendicular to a stack direction between the first and second solid electrolyte bodies 51 and 52.

Figure 3:
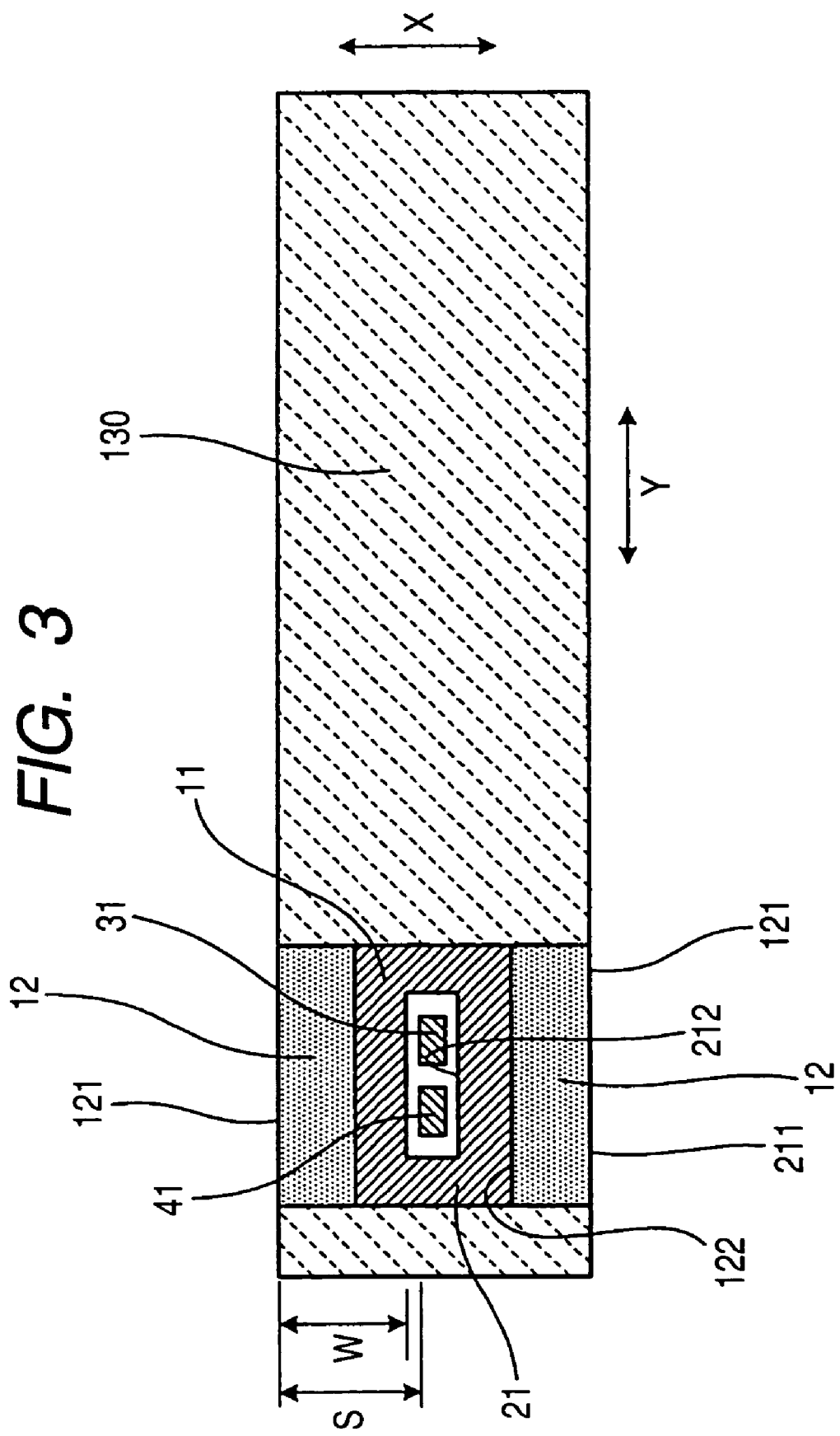
FIG. 3 is a cross sectional view of the gas sensing element taken on line B-B of FIGS. 1 and 2.

As shown in FIG. 3, the measuring electrode 31 is placed in the measuring gas chamber 11 at an area inward of external end walls 211 of the inner pump electrodes 21. In addition, the inner monitor electrode 41 is placed in the measuring gas chamber 11 at an area inward of the external end wall 211 of the inner pump electrodes 21.

With the present embodiment, further, the measuring electrode 31 and the inner monitor electrode 41 are placed inward of the internal end wall 212 of the inner pump electrodes 21.

As shown in FIGS. 1 and 2, the gas sensing element 1 further includes a spacer 130 that is sandwiched between the first and second solid electrolyte bodies 51 and 52 to define the measuring gas chamber 11.

Further, a shielding plate 14 is stacked on the first solid electrolyte body 51 at the other surface in opposition to the measuring gas chamber 11 via a spacer 131 for defining a first reference gas compartment 101.

Furthermore, a spacer 132 is stacked on the second solid electrolyte body 52 at the surface thereof in opposition to the measuring gas chamber 11 for defining a second reference gas compartment 102. A ceramic heater 15 is stacked on the second solid electrolyte body 52 via the spacer 132 for heating the oxygen pump cell 2, the sensor cell 3 and the oxygen monitor cell 4.

The reference electrode 32 of the sensor cell 3 and the outer monitor cell electrode 42 of the oxygen monitor cell 4 are formed in a unitized common electrode, which has a function to act as the reference electrode 32 and the outer monitor cell electrode 42. In addition, the reference electrode 32 and the outer monitor cell electrode 42 are formed on the first solid electrolyte body 51 at the other surface thereof in opposition to the measuring electrode 31 and the inner monitor electrode 41 under a state exposed to the first reference gas compartment 101.

Moreover, the outer pump electrode 22 of the oxygen pump cell 2 is placed on the second solid electrolyte body 52 at the one surface thereof in opposition to the inner pump electrodes 21 under a state exposed to the second reference gas compartment 102.

The measuring electrode 31 and the inner monitor electrode 41 are located on the first solid electrolyte body 51 at the other surface thereof in areas spaced from each other by a given distance along a longitudinal direction Y of the gas sensing element 1. As shown in FIG. 3, further, the inner pump electrode 21 is formed in an encircled area so as to encompass the measuring electrode 31 and the monitor electrode 41.

As shown in FIG. 2, the diffusion resistance portions 12 and the inner pump electrode 21 are placed adjacent to each other in the stack direction Z. The diffusion resistance portions 12 are formed in a pair at both ends of the measuring gas chamber 11 in a widthwise direction X perpendicular to the stack direction Z and the longitudinal direction Y. With the present embodiment, each of the diffusion resistance portions 12 is made of porous body composed of ceramic such as alumina or the like. The diffusion resistance portions 12 are sandwiched between the inner pump electrode 21 and the first solid electrolyte body 51 in overlapping relation to the parts of the inner pump electrode 21 in the stack direction Z.

The measuring electrode 31 is spaced from an external end wall 12 of each diffusion resistance portions 12 by the distance S ranging from 1 to 3 mm.

The first and second solid electrolyte bodies 51 and 52 have principal components such as zirconia and ceria or the like. In addition, the spacers 130, 131 and 132 have principal components made of alumina.

Figure 4:
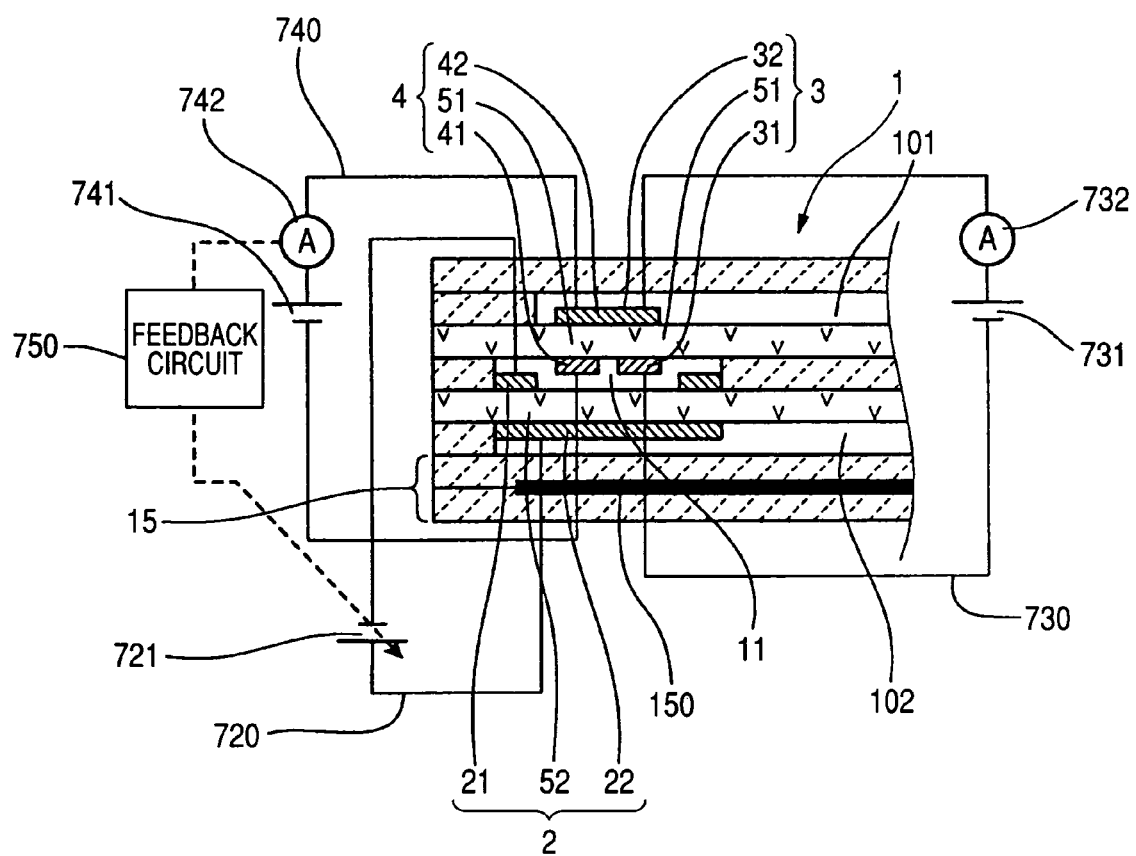
FIG. 4 is an illustrative view showing the gas sensing element of the first embodiment in connection with a sensor circuit, a pump circuit and a monitor circuit.

As shown in FIG. 4, further, the measuring electrode 31 and the reference electrode 32 of the sensor cell 3 are connected to a sensor circuit 730 including a power supply 731 and an ammeter 732.

Furthermore, the measuring electrode 31 and the reference electrode 32 are made of cermet material containing a metallic component having a principal component of Pt and a ceramic component containing a principal component of zirconia. The ceramic component content relative to a total weight of the metallic component and the ceramic component can be determined to lay at a value ranging from, for instance, 10 to 20 wt %.

Further, the measuring electrode 31 includes a Pt—Rh electrode that is active against nitrogen oxides (NOx). The Pt—Rh electrode has an Rh content ranging from, for instance, 10 to 50 wt % relative to a total weight of the metallic component.

As shown in FIG. 4, moreover, the inner pump electrode 21 and the outer pump electrode 22 are connected to a pump circuit 720 including a power supply 721.

Further, like the measuring electrode 31 and the reference electrode 32 of the sensor cell 3, the inner pump electrode 21 and the outer pump electrode 22 are made of cermet material containing the metallic component having the principal component of Pt and the ceramic component containing the principal component of zirconia. The ceramic component content relative to a total weight of the metallic component and the ceramic component can be determined to lay at a value ranging from, for instance, 10 to 20 wt %.

Further, the inner pump electrode 21 is made of a Pt—Au electrode that is inactive against nitrogen oxides. The Au content relative to a total weight of the metallic component ties in a value of, for instance, 1 to 10 wt %.

As shown in FIG. 4, the inner monitor electrode 41 and the outer monitor electrode 42 of the oxygen monitor cell 4 is connected to a monitor circuit 740 including a power supply 741 and an ammeter 742.

Like the measuring electrode 31 and the reference electrode 32 of the sensor cell 3, the inner monitor electrode 41 and the outer monitor electrode 42 are made of cermet material containing the metallic component having the principal component of Pt and the ceramic component containing the principal component of zirconia. The ceramic component content relative to a total weight of the metallic component and the ceramic component can be determined to lay at a value ranging from, for instance, 10 to 20 wt %.

Furthermore, the inner monitor electrode 41 is made of a Pt—Au electrode that is inactive against nitrogen oxides. The Au content relative to a total weight of the metallic component lies in a value of, for instance, 1 to 10 wt %.

As shown in FIG. 4, the oxygen monitor cell 4 includes a feedback circuit 750 that allows an electric current value, measured with the ammeter 742, to be fed back to the oxygen pump cell 2 such that the oxygen pump cell 2 can be controlled in operation. That is, for instance, a control is executed such that if an electric current value, measured with the ammeter 742, exceeds a given value, a voltage of the power supply 721 to be applied to the oxygen pump cell 2, is caused to increase so as to increase a capacity of pumping oxygen delivered from the measuring gas chamber 11 to the second reference gas compartment 102.

Moreover, the measuring electrode 31, the reference electrode 32 (the outer monitor electrode 42), the inner monitor electrode 41, the inner pump electrode 21 and the outer pump electrode 22 are electrically connected to external terminals via electrically conductive lead portions and through-holes (not shown).

As shown in FIGS. 1 and 2, the ceramic heater 15 includes a heater substrate 151, an insulating layer 152 stacked on the heater substrate 151, and a heating element 150 sandwiched between the heater substrate 151 and the insulating layer 152.

With the ceramic heater 15, further, the heating element 150, operative to heat when turned on, and a lead portion 153, connected thereto, are formed on a sheet made of alumina by patterning and the insulating layer 152 is placed on the heating element 150. The heating element 150 is made of cermet material composed of ceramic such as, for instance, Pt and alumina or the like.

The ceramic heater 15 serves to allow the heating element 150 to develop a heat when supplied with electric power from the outside for heating the oxygen pump cell 2, the sensor cell 3 and the oxygen monitor cell 4 to active temperatures.

The heating element 150 is supplied with electric power via the lead portion 153 integrally formed on the heating element 150, the through-holes (not shown) and the terminals portions (not shown).

Moreover, the first and second solid electrolyte bodies 51 and 52, the spacers 130, 131 and 132, a shielding plate 14, the insulating layer 152 and the heater substrate 151 can be formed in sheet-like members by a doctor blade method or an extrusion molding method or the like.

Further, the measuring electrode 31, the reference electrode 32, the inner monitor electrode 41, the outer monitor electrode 42, the inner pump electrode 21 and the outer pump electrode 22 can be formed by a screen printing method or the like.

Furthermore, a porous body, forming the diffusion resistance portions 12, can be formed by a screen-printing method or the like.

Moreover, the gas sensing element 1 can be formed by stacking ceramic sheets, suitably formed with the various electrodes mentioned above, to form a stack body upon which the stack body is fired in a unitized structure.

Next, an operating principle of the gas sensing element 1 will be described below.

First, measuring gases pass through the diffusion resistance portions 12 under given diffusion resistances to be introduced into the measuring gas chamber 11. The amount of admitted measuring gases is determined in accordance with diffusion resistances of the diffusion resistance portions 12. During a transfer of measuring gases through surface of the inner pump electrode 21 of the oxygen pump cell 2, the oxygen concentration of measuring gases is adjusted with the oxygen pump cell 2.

That is, applying a voltage across a pair of electrodes of the oxygen pump cell 2 to allow the outer pump electrode 22 to act as a positive electrode results in an effect of causing oxygen, contained in measuring gases, to be reduced on the inner pump electrode 21 to form an oxygen ion. The oxygen ion is discharged to the outer pump electrode 22 exposed to the reference gas compartment 102 due to a pumping action. In contrast, if the voltage is applied so as to allow the inner pump electrode 21 to be positive electrode, then, reduction of oxygen occurs on the outer pump electrode 22 to form oxygen ions, which are discharged to the inner pump electrode 21 exposed to the measuring gas chamber 11 due to a pumping action. That is, the oxygen pump cell 2 is structured such that with a voltage applied to the pair of electrodes, the oxygen pump cell 2 allows oxygen to flow into or flow out from the measuring gas chamber 11 for adjusting an oxygen concentration in the measuring gas chamber 11.

Particularly, during the flow of measuring gases through the diffusion resistance portions 12, it is likely that measuring gases tend to be easily brought into contact with the inner pump electrode 21, resulting in a consequence of easily adjusting the oxygen concentration.

Subsequently, measuring gases passing across the inner pump electrode 21 reach the measuring electrode 31 of the sensor cell 3 and the inner monitor electrode 41 of the oxygen monitor cell 4.

With a given voltage (of, for instance, 0.40V) being applied across the pair of electrodes of the oxygen monitor cell 4 such that the outer monitor electrode 42, exposed to the first reference gas compartment 101, becomes a positive electrode, a reduction of oxygen in measuring gases occurs on the inner monitor electrode 41 exposed to the first reference gas compartment 101, thereby forming oxygen ions. The oxygen ions are discharged to the outer monitor electrode 42 exposed to the measuring gas chamber 11 due to a pumping action for thereby causing an oxygen ion current to flow.

Here, since the inner monitor electrode 41 is comprised of the cermet electrode made of Pt—Au alloy that is inactive in decomposing nitrogen oxides, the oxygen ion current, flowing through the oxygen monitor cell 4, depends on the amount of oxygen contained in measuring gases and does not depend on the amount of nitrogen oxides. This allows a value of the electric current, flowing through the oxygen monitor cell 4, to be detected, thereby enabling the detection of the oxygen concentration in the measuring gas chamber 11.

Further, the gas sensing element 1 of the present embodiment is structured to control the oxygen pump cell 2 via the feedback circuit 750 so as to allow the measuring gas chamber 11 to have the oxygen concentration laying at a given fixed value in accordance with a detected value of the electric current flowing through the oxygen monitor cell 4. That is, controlling a voltage applied to the oxygen pump cell 3 in response to an output signal from the oxygen monitor cell 4 so as to allow the oxygen monitor cell 4 to provide an electric current value laying at a desired fixed value (of, for instance, 0.2 µA) results in a capability of controlling the oxygen concentration of the measuring gas chamber 11 at a fixed value.

Furthermore, a given voltage (of, for instance, 0.40V) is applied to the sensor cell 3 such that the reference electrode 32, exposed to the first reference gas compartment 101, becomes a positive electrode. As set forth above, since the measuring electrode 31 is comprised of the cermet electrode made of Pt—Rh alloy that is active in decomposing nitrogen oxides, reductions of oxygen and nitrogen oxides, contained in measuring gases prevailing in the measuring gas chamber 11, occur on the measuring electrode 31 to form oxygen ions. The oxygen ions are discharged to the reference electrode 32 exposed to the first reference gas compartment 101 due to a pumping action for thereby causing an oxygen ion current to flow across the measuring electrode 31 and the reference electrode 32. This electric current represents an electric current derived from concentrations of NOx and oxygen contained in measuring gases.

Meanwhile, as mentioned above, the electric current flowing through the oxygen monitor cell 4 represents an electric current resulting form the oxygen concentration in the measuring gas chamber 11. Thus, it becomes possible to detect a NOx concentration based on a difference between a value of electric current flowing through the sensor cell 3 and a value of electric current flowing through the oxygen monitor cell 4.

The gas sensing element 1 operates in a manner as described below.

The diffusion resistance portions 12 are formed on the first solid electrolyte body 51 so as to extend from the measuring gas chamber 11 in a direction perpendicular to the stack direction Z between the first and second solid electrolyte bodies 51 and 52. This allows a distance S between the external end wall 121 of the diffusion resistance portions 12, i.e., an inlet port of measuring gases, and the measuring electrode 31 to be shortened, enabling an increase in response of the gas sensing element 1.

With the gas sensing element 1 of the present embodiment, the diffusion resistance portions 12 are formed on the first solid electrolyte body 51 in areas extending along the widthwise direction X perpendicular to the longitudinal direction Y of the gas sensing element 1. This easily results in an effect of deceasing the distance S between the external end wall 121 of each diffusion resistance portion 12, i.e., the inlet port of measuring gases, and the measuring electrode 31. Thus, the gas sensing element 1 can have further increased response.

Moreover, the measuring electrode 31 is formed on the first solid electrolyte body 51 in an area inward of the external end wall 211 of the inner pump electrode 21. This allows the oxygen pump cell 2 to adjust the oxygen concentration in measuring gases before measuring gases reach the measuring electrode 31. Therefore, the gas sensing element 1 can have increased measuring precision.

With the gas sensing element 1 of the present embodiment, especially, the measuring electrode 31 is formed on the first solid electrolyte body 51 in an area inward of an inner end wall 212 of the inner pump electrode 21. This allows the oxygen concentration to be adequately adjusted with the oxygen pump cell 2 and, subsequently, measuring gases with the oxygen concentration being adjusted can be supplied to the measuring electrode 31. Thus, the gas sensing element 1 can have increased precision in measuring a specified gas concentration.

Further, the diffusion resistance portions 12 and the inner pump electrodes 21 are disposed adjacent to each other in the stack direction. Therefore, measuring gases can be adequately held in contact with the inner pump electrodes 21 during a phase in which measuring gases pass across the diffusion resistance portions 12 to be admitted to the measuring gas chamber 11. During such a phase, therefore, the oxygen pump cell 2 can adequately pump oxygen, thereby enabling the oxygen concentration in measuring gases to be adequately adjusted.

Furthermore, with the gas sensing element 1 provided with the oxygen monitor cell 4, the oxygen concentration in the measuring gas chamber 11 can be accurately grasped to obtain a measured result. Permitting the measured result to be used in a feedback control for controlling the oxygen pump cell 2 while causing the measured result to be used in correcting the measured value of the sensor cell 3, enables an increase in measuring precision. In addition, the inner monitor electrode 41 is placed in an area inward of the external end wall 211 of the inner pump electrode 21. This enables the oxygen monitor cell 4 to accurately measure the oxygen concentration of measuring gases whose oxygen concentration is adjusted with the oxygen pump cell 2.

In particular, if an attempt is made to decrease the distance S between the external end wall 121 of each diffusion resistance portion 12 and the measuring electrode 31 to obtain improved response, then, there is a risk of a difficulty occurring in adequately ensuring oxygen pumping capability. Therefore, providing the oxygen monitor cell 4 results in capabilities of minimizing the fluctuation in oxygen concentration in the measuring gas chamber 11 and correcting the measured value. Thus, it becomes possible to secure precision of detecting a specified gas concentration (NOx concentration).

With the gas sensing element 1 of the present embodiment, moreover, the inner monitor electrode 41 is disposed in an area inward of the inner end wall 212 of the inner pump electrode 21. This enables measuring gases, whose oxygen concentration is adequately adjusted with the oxygen pump cell 2, to be supplied to the inner monitor electrode 41, thereby enabling an increase in precision of measuring the oxygen concentration.

Further, the gas sensing element 1 of the present embodiment is structured such that a voltage applied to the oxygen pump cell 2 is controlled in response to a detection signal on the oxygen concentration in the oxygen monitor cell 4. This allows the oxygen concentration to be sustained at a fixed value in the measuring gas chamber 11. Especially, if an attempt is made to decrease the distance S between the external end wall 121 of the diffusion resistance portions 12 and the measuring electrode 31 to obtain improved response, then, the inner pump electrode 21 tends to have a decreased width W, causing a risk of a difficulty in adequately ensuring oxygen pumping capability. Therefore, permitting the oxygen monitor cell 4 to monitor the oxygen concentration in the measuring gas chamber 11 while causing a resulting detection signal to be supplied to the oxygen pump cell 2 in a feedback loop, enabling the oxygen concentration to be easily adjusted.

Furthermore, the oxygen monitor cell 4 is structured such that when a given voltage is applied across the inner monitor electrode 41 and the outer monitor electrode 42, an electric current is caused to flow depending on the oxygen concentration in measured gases. Further, another arrangement is made such that a specified gas concentration (NOx concentration) is detected depending on a difference between an electric current flowing through the sensor cell 3 and an electric current flowing through the oxygen monitor cell 4. This enables the measured value of the specified gas concentration (NOx concentration) in the sensor cell 3 to be corrected, making it possible to obtain an accurate measuring value.

Further, since the dispersion resistance portions 12 are made of the porous body, diffusion resistance can be easily adjusted.

Furthermore, the shortest distance S between the external end wall 121 of the diffusion resistance portions 12 and the measuring electrode 31 is set to a value ranging from 1 to 3 mm. This results in a capability of obtaining the gas sensing element 1 with adequately improved response while ensuring adequately improved measuring precision.

With the present embodiment, as set forth above, it becomes possible to provide a gas sensing element with excellent response and increased measuring precision.

Second Embodiment

Figure 5:
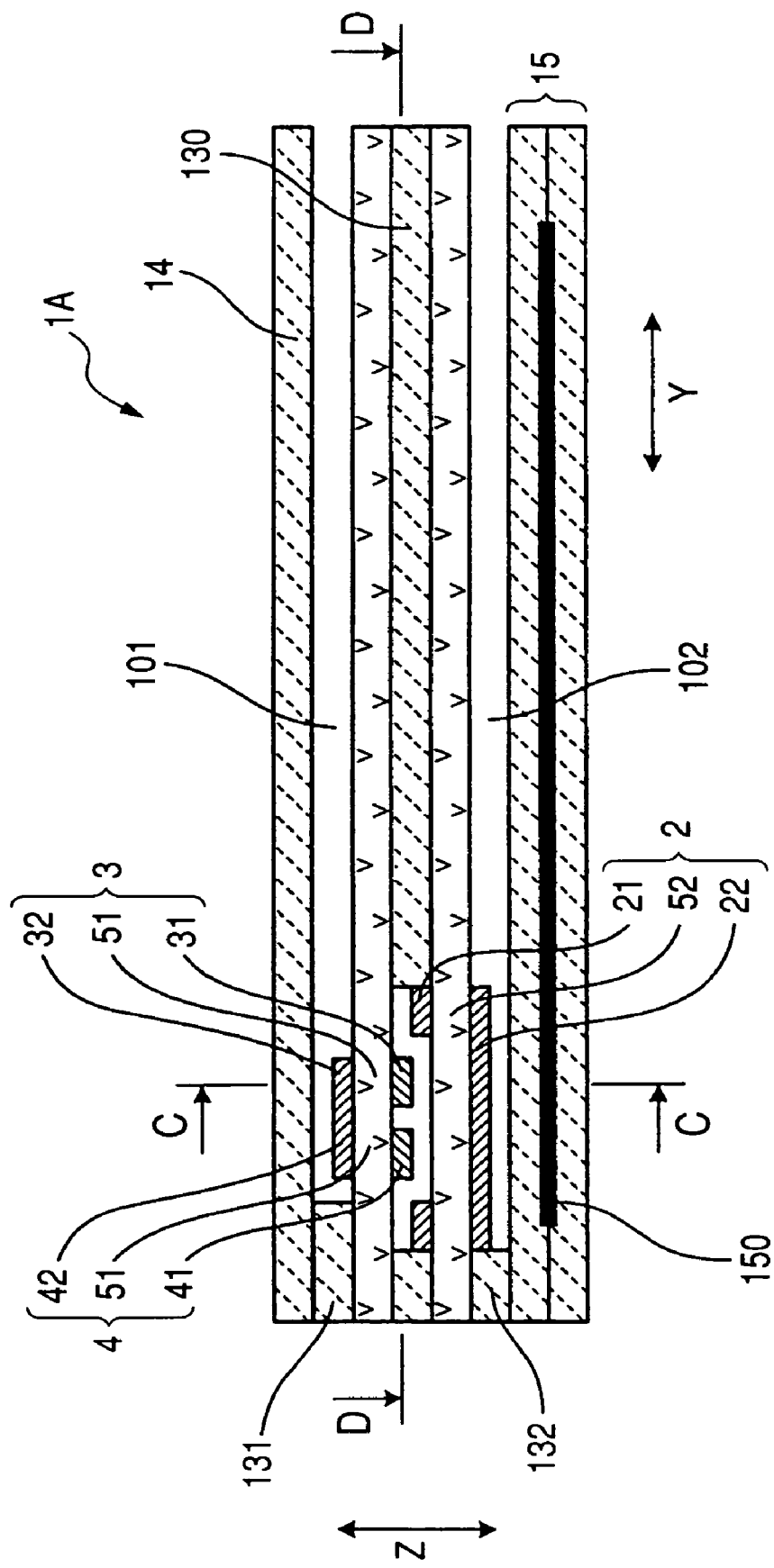
FIG. 5 is a view showing a gas sensing element of a second embodiment according to the present invention in cross section taken on a plane parallel to the longitudinal direction Y and the stack direction Z.
Figure 6:
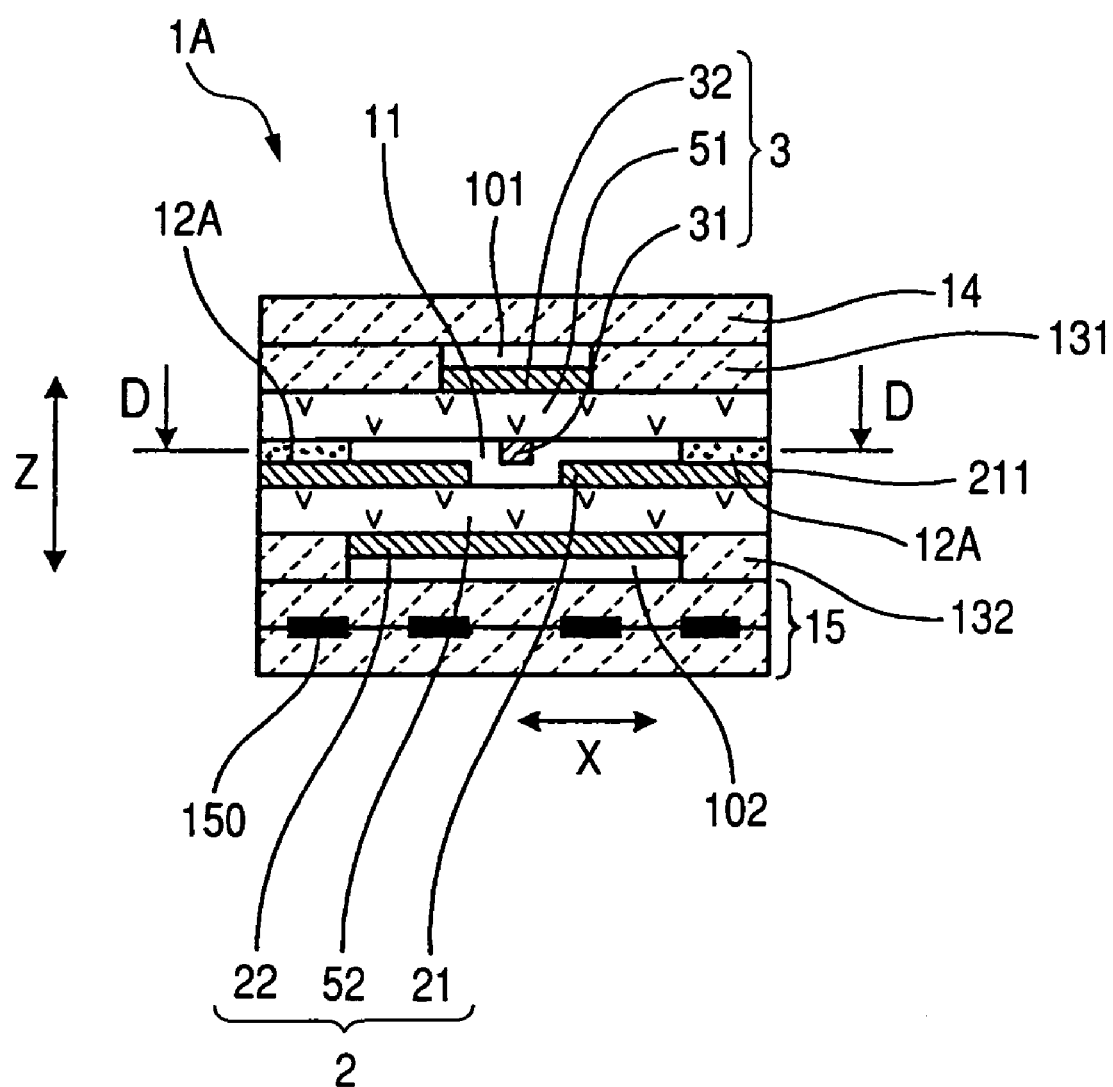
FIG. 6 is a cross sectional view of the gas sensing element taken on line C-C of FIG. 5.
Figure 7:
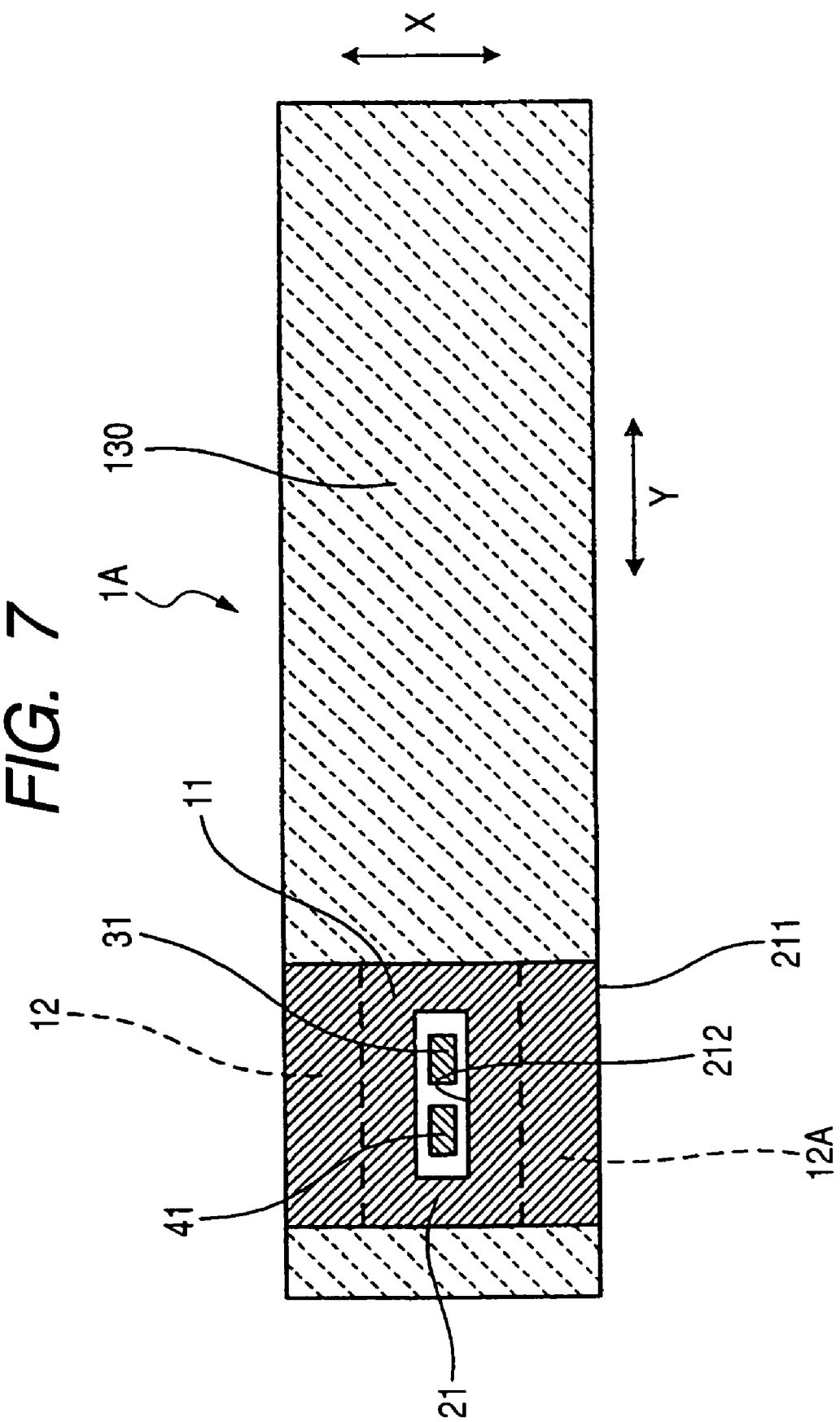
FIG. 7 is a cross sectional view of the gas sensing element taken on line D-D of FIGS. 5 and 6.

A gas sensing element 1A of a second embodiment will be described below in detail with reference to FIGS. 5 to 7 with like component parts bearing the same reference numerals as those of the gas sensing element 1 of the first embodiment shown in FIGS. 1 to 4.

The gas sensing element 1A of the second embodiment differs from the gas sensing element 1 of the first embodiment in respect of structures of gas diffusion resistance portions 12A. That is, with the gas sensing element 1A of the second embodiment, the gas diffusion resistance portions 12A are not made of porous bodies, used for the gas diffusion resistance portions 12 of the gas sensing element 1 of the first embodiment, but are formed of slits with minimized clearances. The slits are formed in structure by suitably adjusting a thickness in the stack direction Z so as to obtain desired diffusion resistances. This thickness can be set to a value of, for instance, 5 to 50 μm.

The gas sensing element 1A of the second embodiment has the same other structure as that of the gas sensing element 1 of the first embodiment.

With the gas sensing element 1A of the present modification, there is no need arising for performing step of forming a porous body, thereby achieving a reduction in production cost.

In addition, the gas sensing element 1A of the present modification performs the same operation as that of the gas sensing element 1 of the first embodiment and, hence, detailed description of the same is herein omitted.

Third Embodiment

Figure 8:
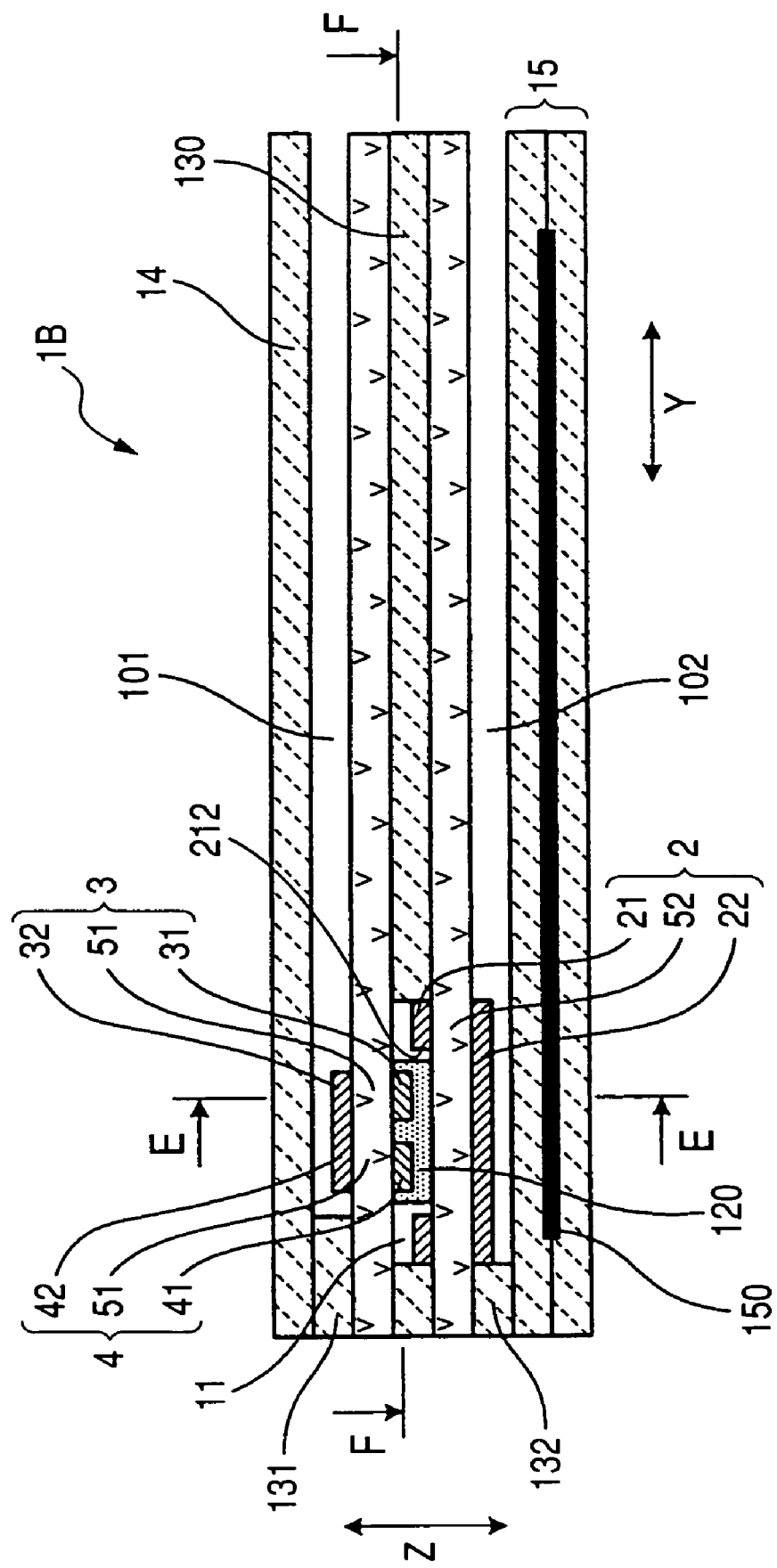
FIG. 8 is a view showing a gas sensing element of a third embodiment according to the present invention in cross section taken on a plane parallel to the longitudinal direction Y and the stack direction Z.
Figure 9:
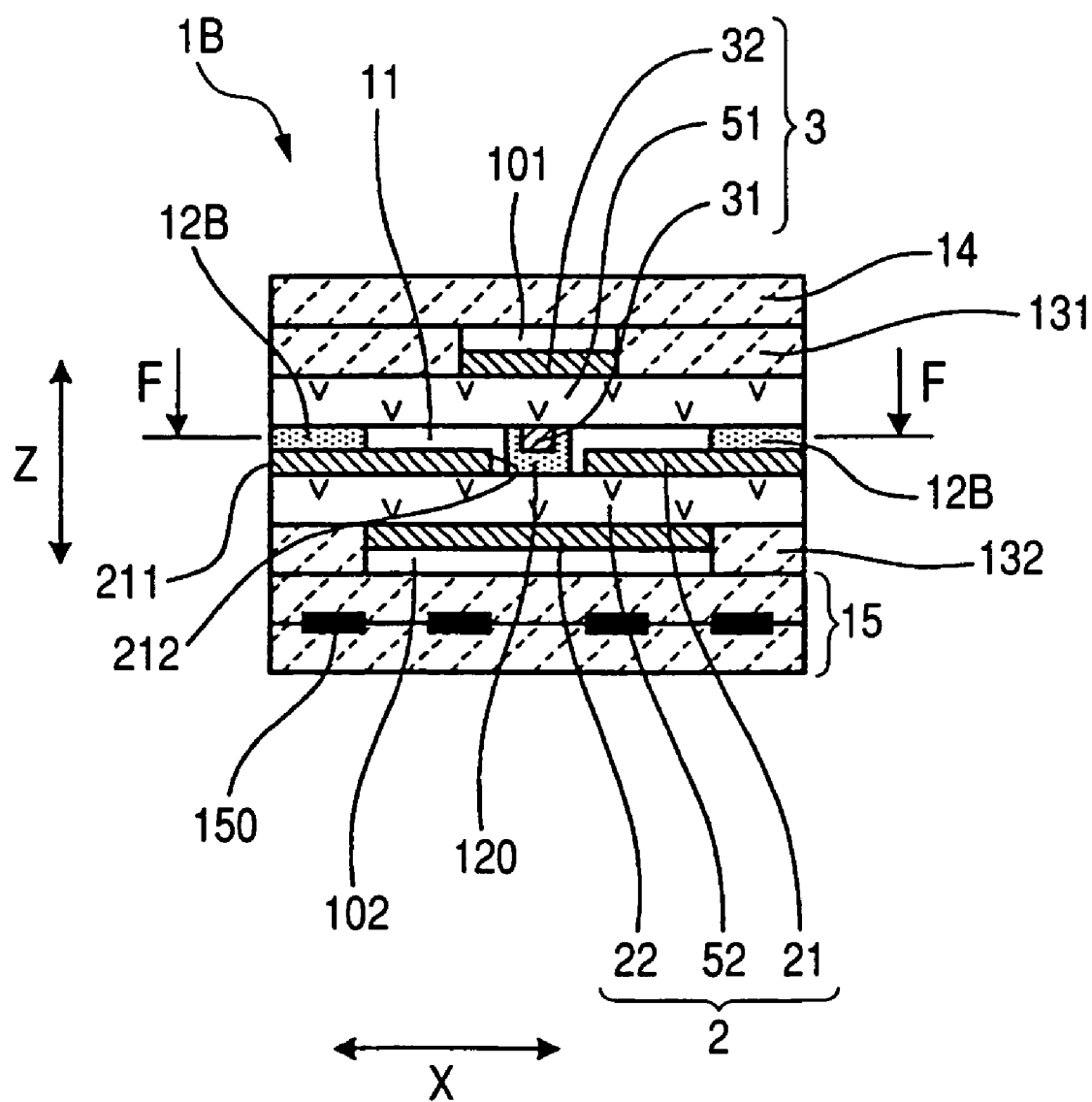
FIG. 9 is a cross sectional view of the gas sensing element taken on line E-E of FIG. 8.
Figure 10:
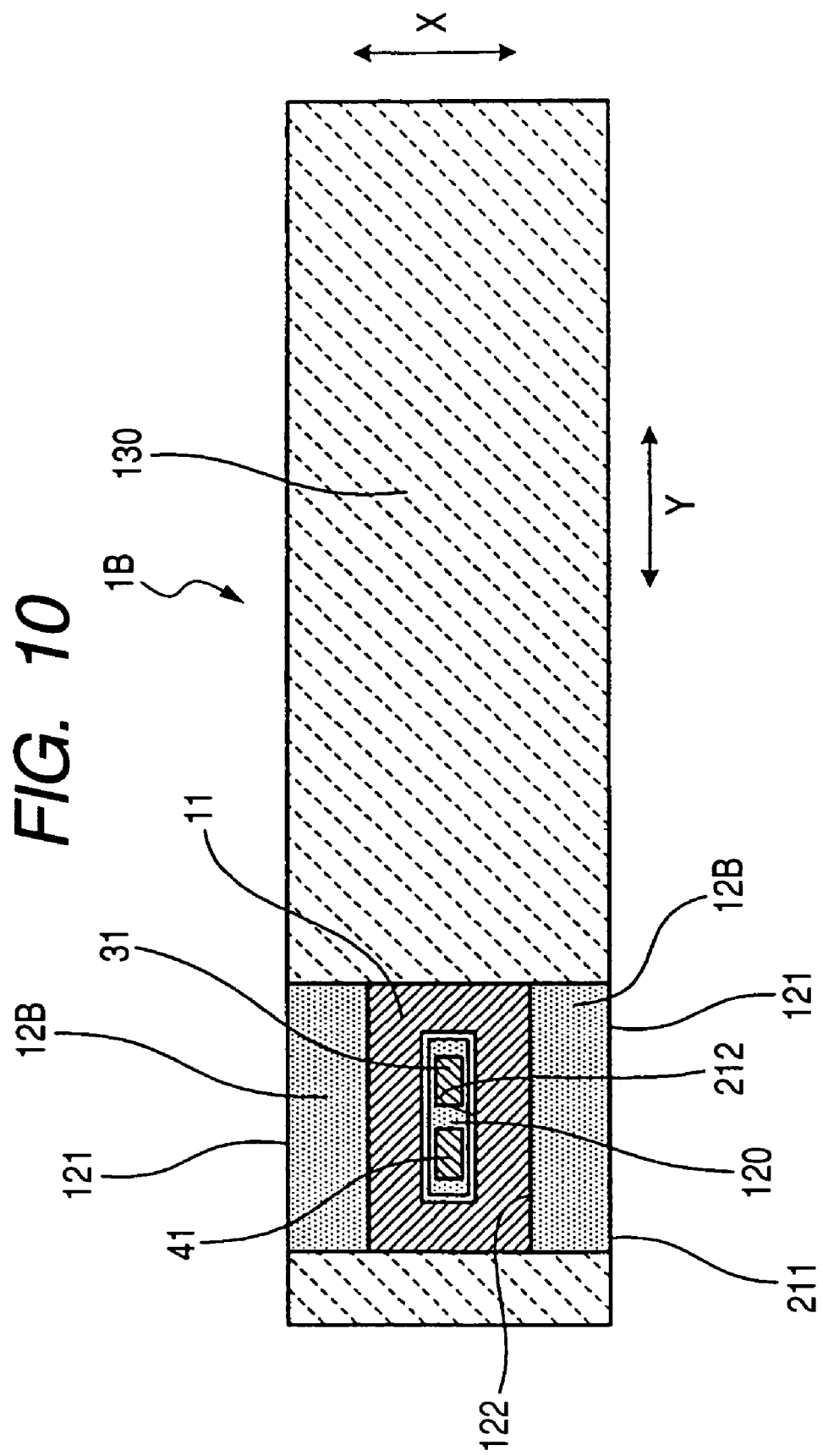
FIG. 10 is a cross sectional view of the gas sensing element taken on line F-F of FIGS. 8 and 9.

A gas sensing element 1B of a third embodiment will be described below in detail with reference to FIGS. 8 to 10 with like component parts bearing the same reference numerals as those of the gas sensing element of the first embodiment shown in FIGS. 1 to 4.

The gas sensing element 1B of the third embodiment differs from the gas sensing element 1 of the first embodiment in that a gas diffusion resistance portion 120 is provided between the measuring electrode 31 and the inner pump electrode 21 for providing diffusion resistance for measuring gases.

The gas diffusion resistance portion 120 is comprised of a porous body, made of ceramic such as alumina or the like, which is formed so as to cover both the measuring electrode 31 and the oxygen monitor electrode 41. In addition, the gas diffusion resistance portion 120 is located in an area inward of the inner end wall 212 of the inner pump electrode 21.

The gas sensing element 1B of the third embodiment has the same other structure as that of the gas sensing element 1 of the first embodiment.

With the gas sensing element 1B of the present modification, measuring gases, first adjusted with the oxygen pump cell 2 in adequate oxygen concentration, can be supplied to the measuring electrode 31, enabling a specified gas concentration to be detected with improved precision.

The gas sensing element 1B of the present modification performs the same operation as that of the gas sensing element 1 of the first embodiment and, hence, detailed description of the same is herein omitted.

Fourth Embodiment

Figure 11:
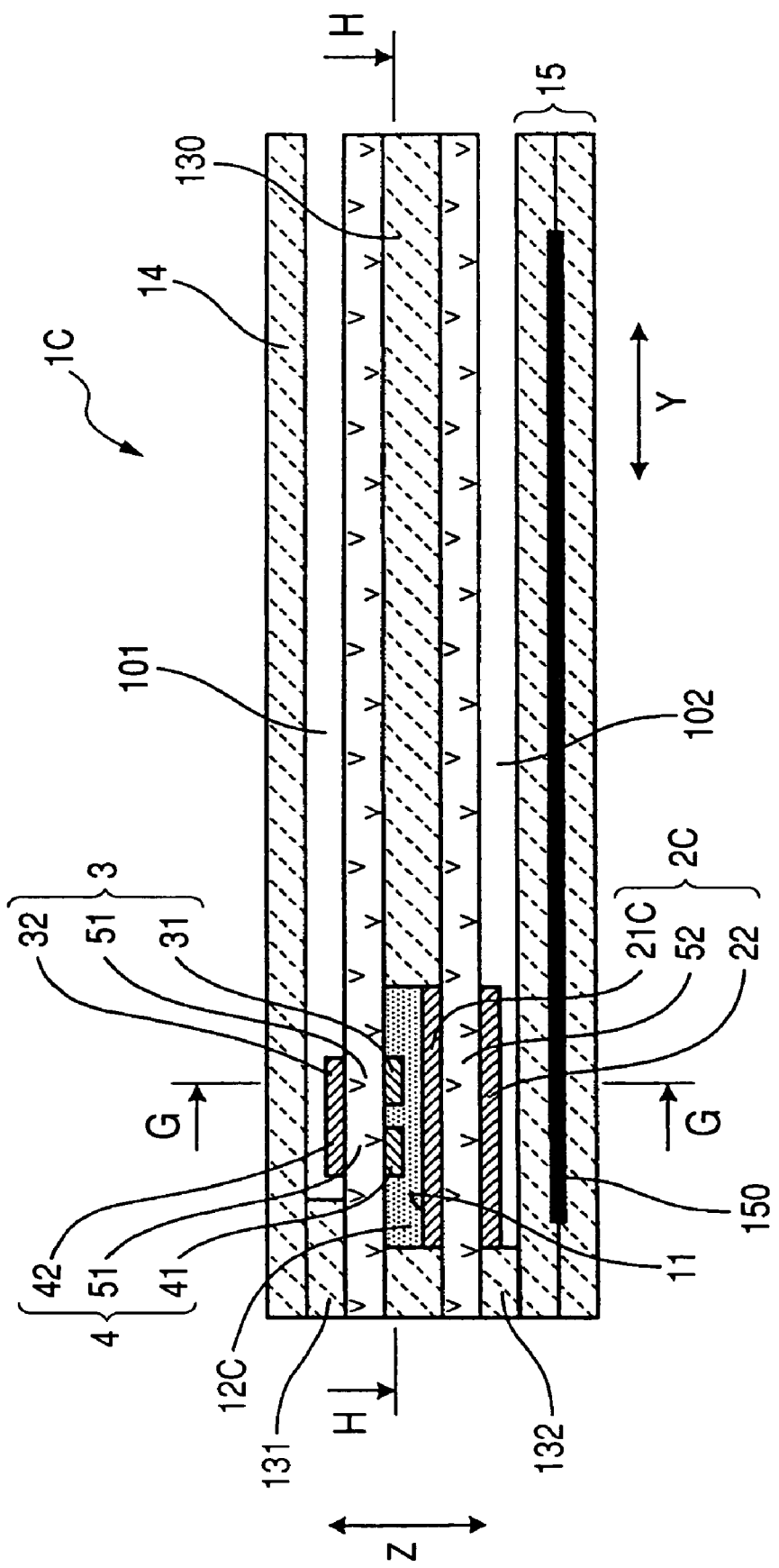
FIG. 11 is a view showing a gas sensing element of a fourth embodiment according to the present invention in cross section taken on a plane parallel to the longitudinal direction Y and the stack direction Z.
Figure 12:
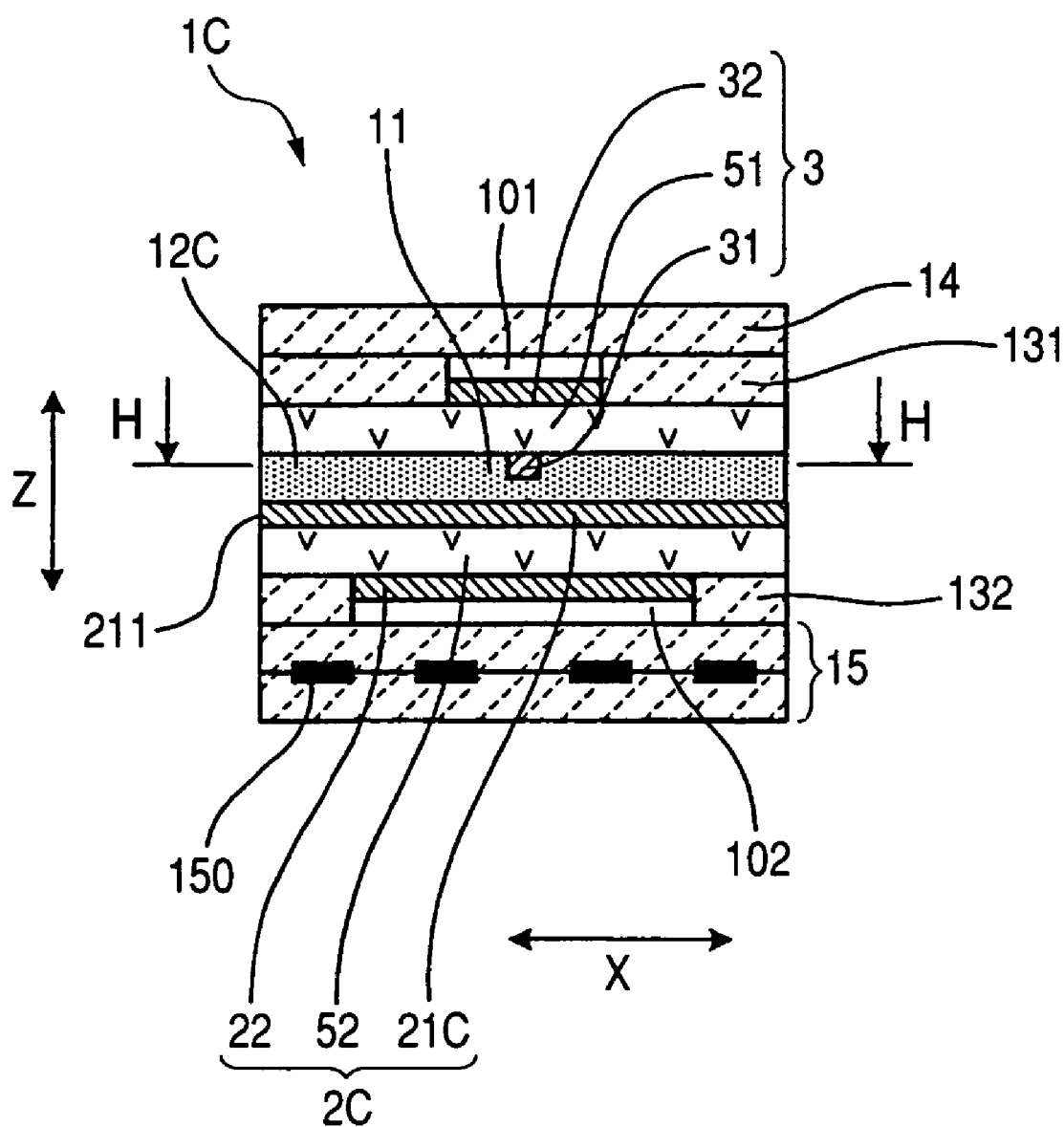
FIG. 12 is a cross sectional view of the gas sensing element taken on line G-G of FIG. 11.
Figure 13:
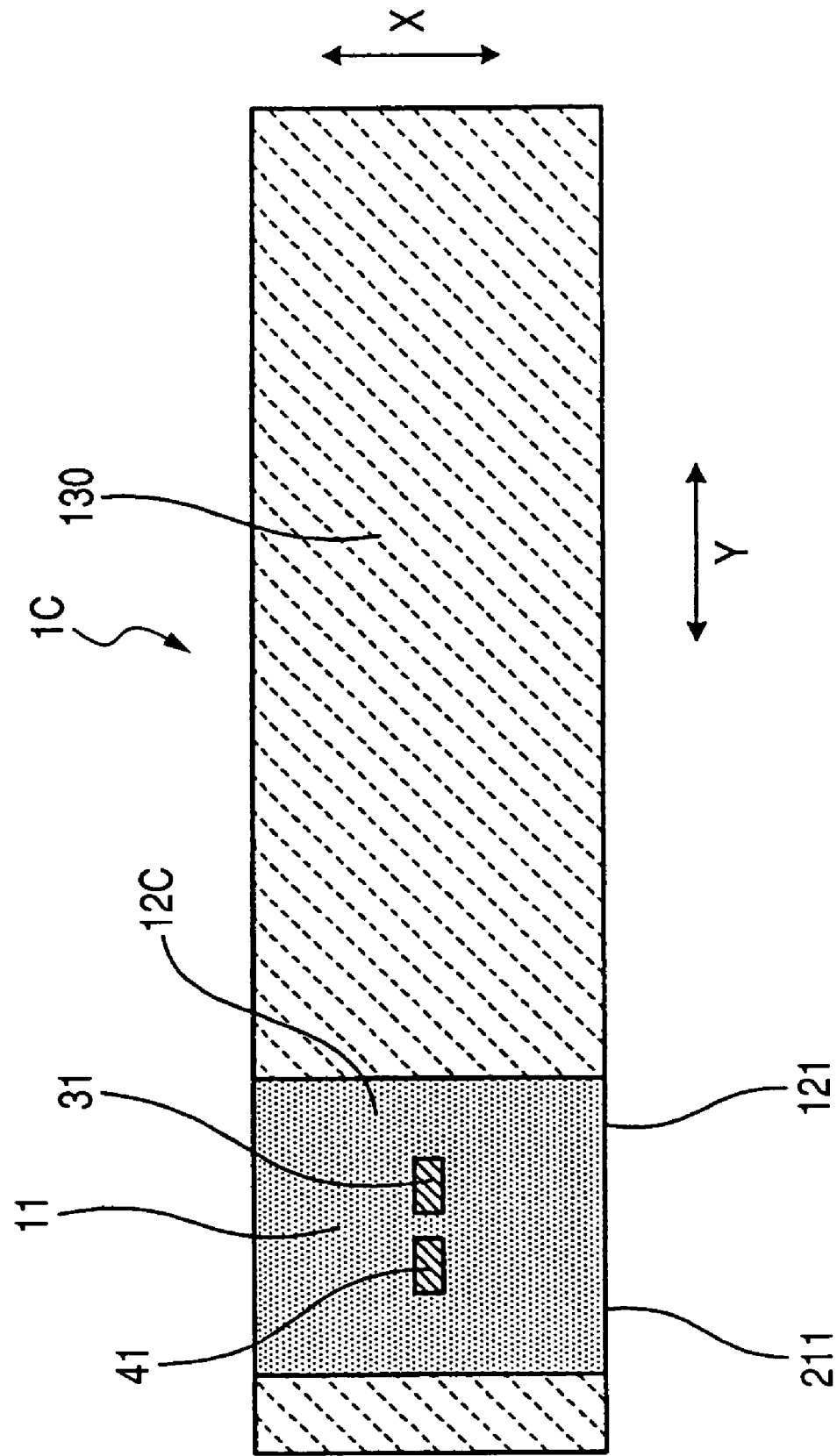
FIG. 13 is a cross sectional view of the gas sensing element taken on line H-H of FIGS. 11 and 12.

A gas sensing element 1C of a fourth embodiment will be described below in detail with reference to FIGS. 11 to 13 with like component parts bearing the same reference numerals as those of the gas sensing element of the first embodiment.

The gas sensing element 1C of the fourth embodiment differs from the gas sensing element 1 of the first embodiment in that an oxygen pump cell 2C has an inner pump electrode 21C formed on the second solid electrolyte body 52 in a whole surface area facing the measuring gas chamber 11 and a gas diffusion resistance portions 12C is formed in a whole area of the measuring gas chamber 11 so as to cover the measuring electrode 31 and the inner monitor electrode 41 for providing diffusion resistance for measuring gases.

The gas sensing element 1C of the present embodiment has the same other structure as that of the gas sensing element 1 of the first embodiment With the gas sensing element 1C of the present modification, the oxygen pump cell 2C can easily adjust the oxygen concentration in the measuring gas chamber 11.

The gas sensing element 1C of the present modification performs the same operation as that of the gas sensing element 1 of the first embodiment and, hence, detailed description of the same is herein omitted.

Fifth Embodiment

Figure 14:
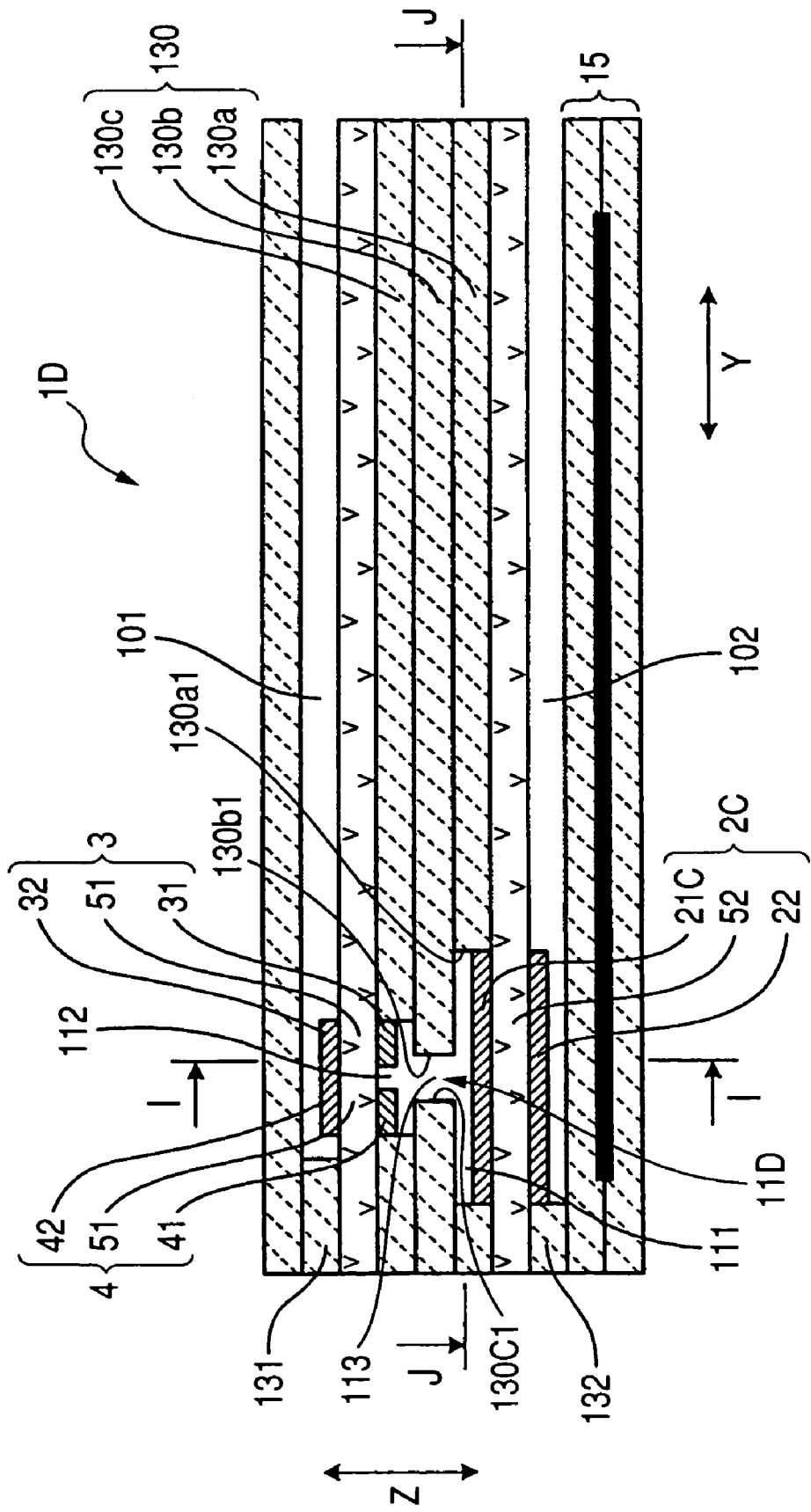
FIG. 14 is a view showing a gas sensing element of a fifth embodiment according to the present invention in cross section taken on a plane parallel to the longitudinal direction Y and the stack direction Z.
Figure 15:
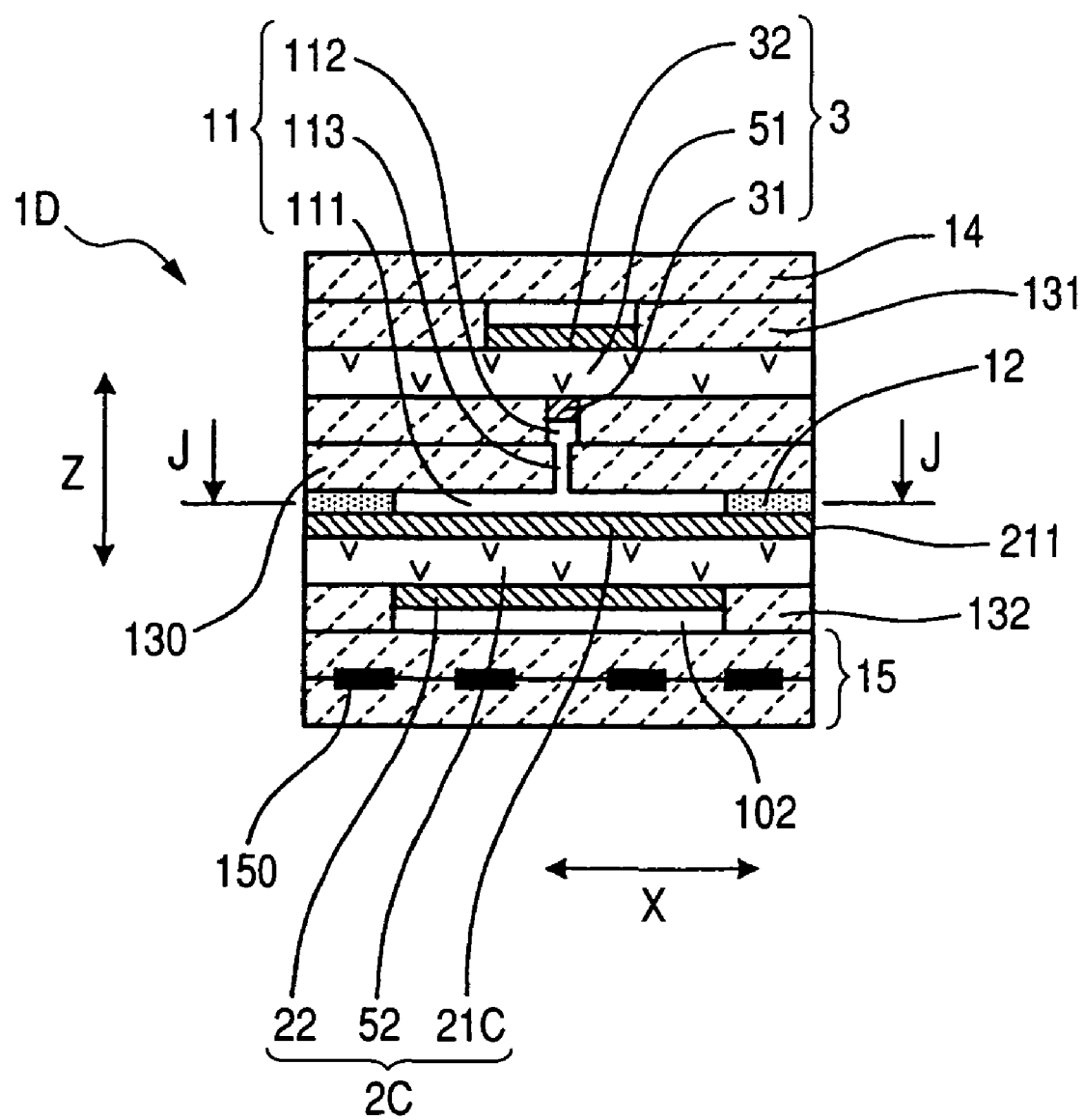
FIG. 15 is a cross sectional view of the gas sensing element taken on line I-I of FIG. 14.
Figure 16:
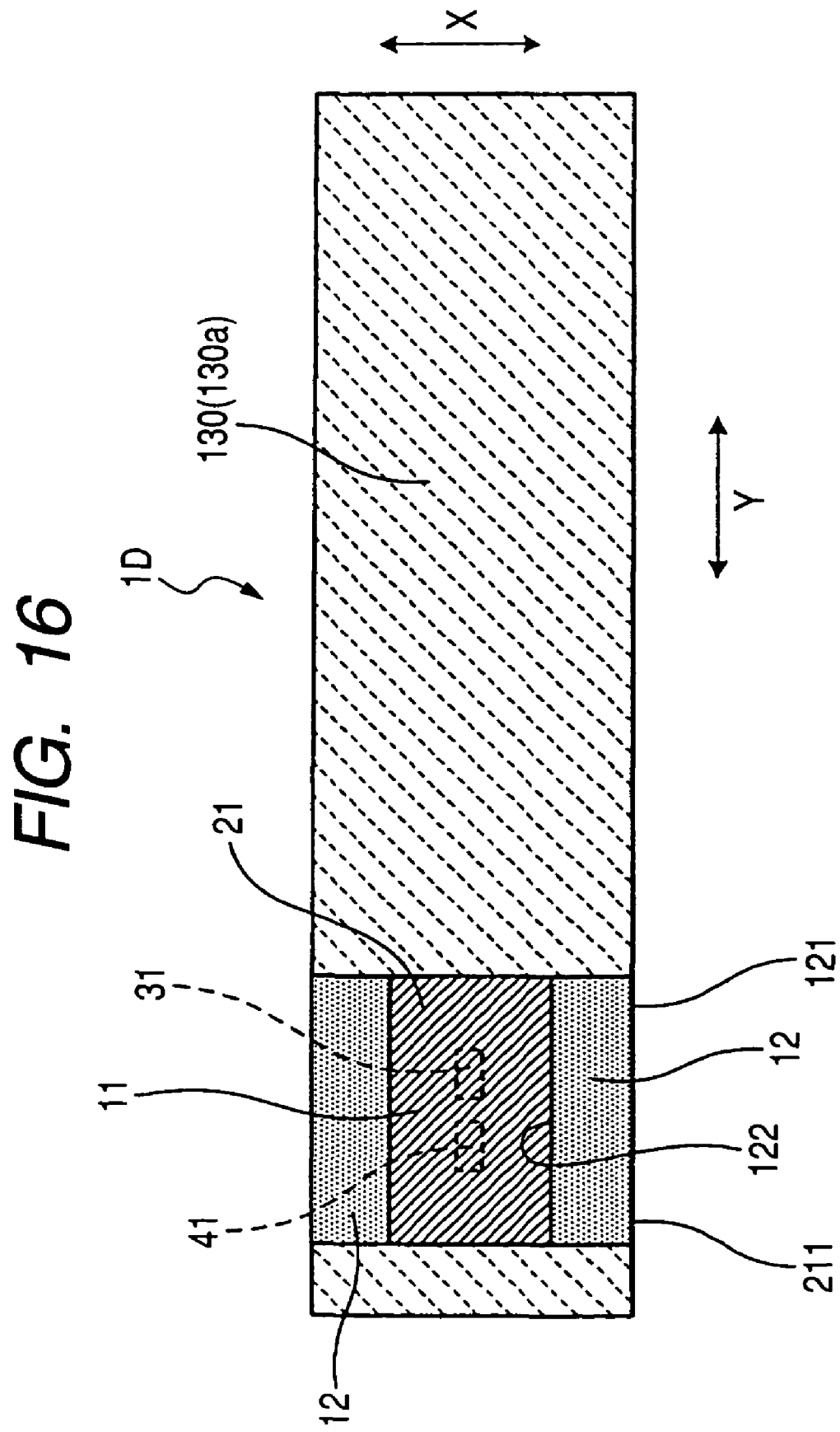
FIG. 16 is a cross sectional view of the gas sensing element taken on line J-J of FIGS. 14 and 15.

A gas sensing element 1D of a fifth embodiment will be described below in detail with reference to FIGS. 14 to 16 with like component parts bearing the same reference numerals as those of the gas sensing element 1C of the fourth embodiment mentioned above.

The gas sensing element 1D of the fifth embodiment differs from the gas sensing element 1C of the fourth embodiment in that a measuring gas chamber 11D includes a first measuring gas chamber 111 and a second measuring gas chamber 112 which communicate each other via a restricted portion 213 and the inner pump electrode 21C faces the first measuring gas chamber 111 while the measuring electrode 31 and the inner monitor electrode 41 face the second measuring gas chamber 112. In addition, the inner pump electrode 21C is formed on the second solid electrolyte body 52 in a whole surface area thereof at a position placed facing the first measuring gas chamber 111.

A spacer 130, provided between the first and second solid electrolyte bodies 51 and 52, includes ceramic layers 130a, 130b and 130c in three layers having cutout portions formed at different positions. The ceramic layer 130a has a first cutout portion 130a1 with which the first measuring gas chamber 111 is defined. Likewise, the ceramic layer 130b has a second cutout portion 130b1 with which the restricted portion 113 is defined. Likewise, the ceramic layer 130c has a third cutout portion 130c1 with which the second measuring gas chamber 112 is defined.

The gas sensing element 1D of the present embodiment has the same other structure as that of the gas sensing element 1 of the first embodiment.

With the gas sensing element 1D of the present modification, measuring gases are admitted through the diffusion resistance portions 12 to the first measuring gas chamber 111 in which the oxygen pump cell 2C adjusts the oxygen concentration. Thereafter, measuring gases pass across the restricted portion 113 to flow into the second measuring gas chamber 112, in which the sensor cell 3 detects a specified gas concentration and the oxygen monitor cell 4 detects an oxygen concentration.

Therefore, it becomes possible to obtain the gas sensing element 1D with further excellent measuring precision.

The gas sensing element 1D of the present modification performs the same operation as that of the gas sensing element 1 of the first embodiment and, hence, detailed description of the same is herein omitted.

Sixth Embodiment

Figure 17:
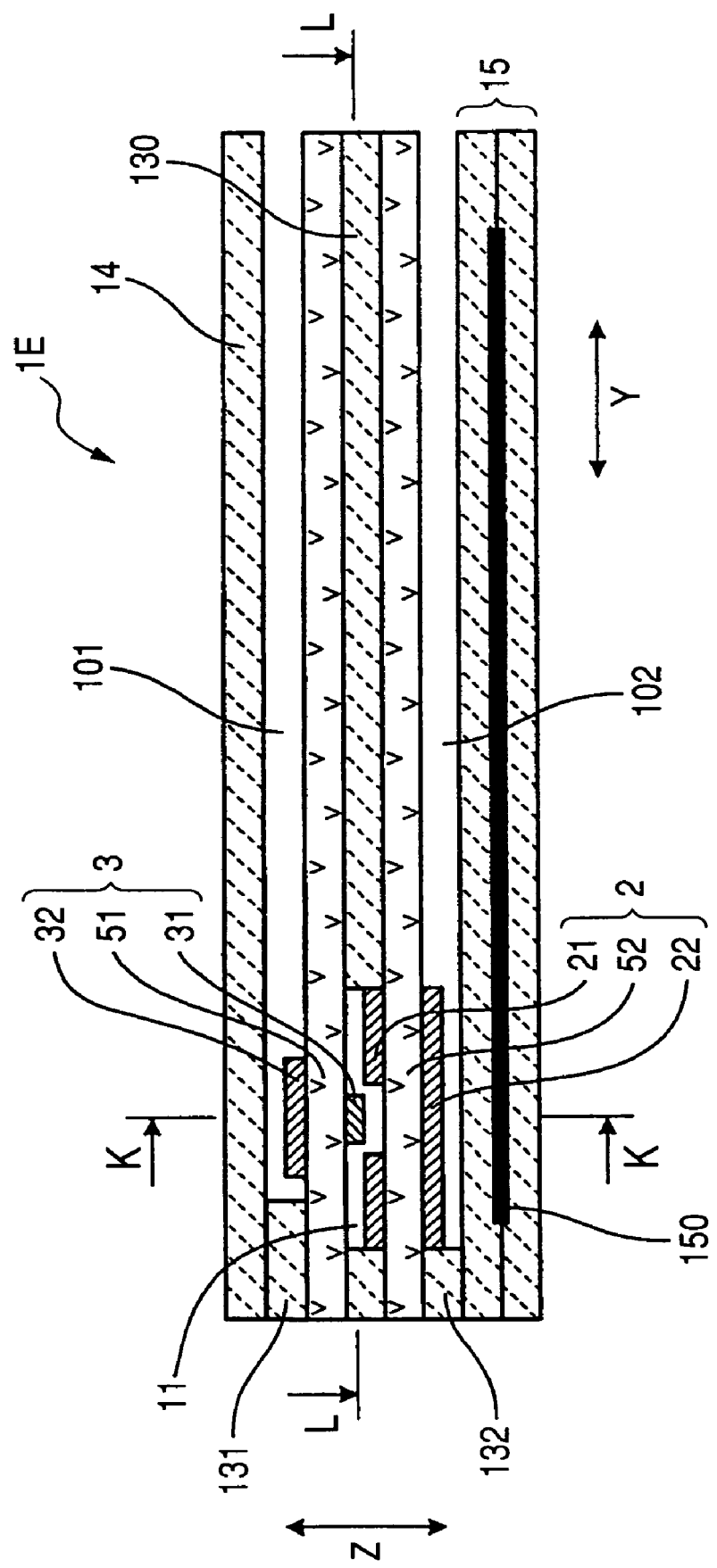
FIG. 17 is a view showing a gas sensing element of a sixth embodiment according to the present invention in cross-section taken on a plane parallel to the longitudinal direction Y and the stack direction Z.
Figure 18:
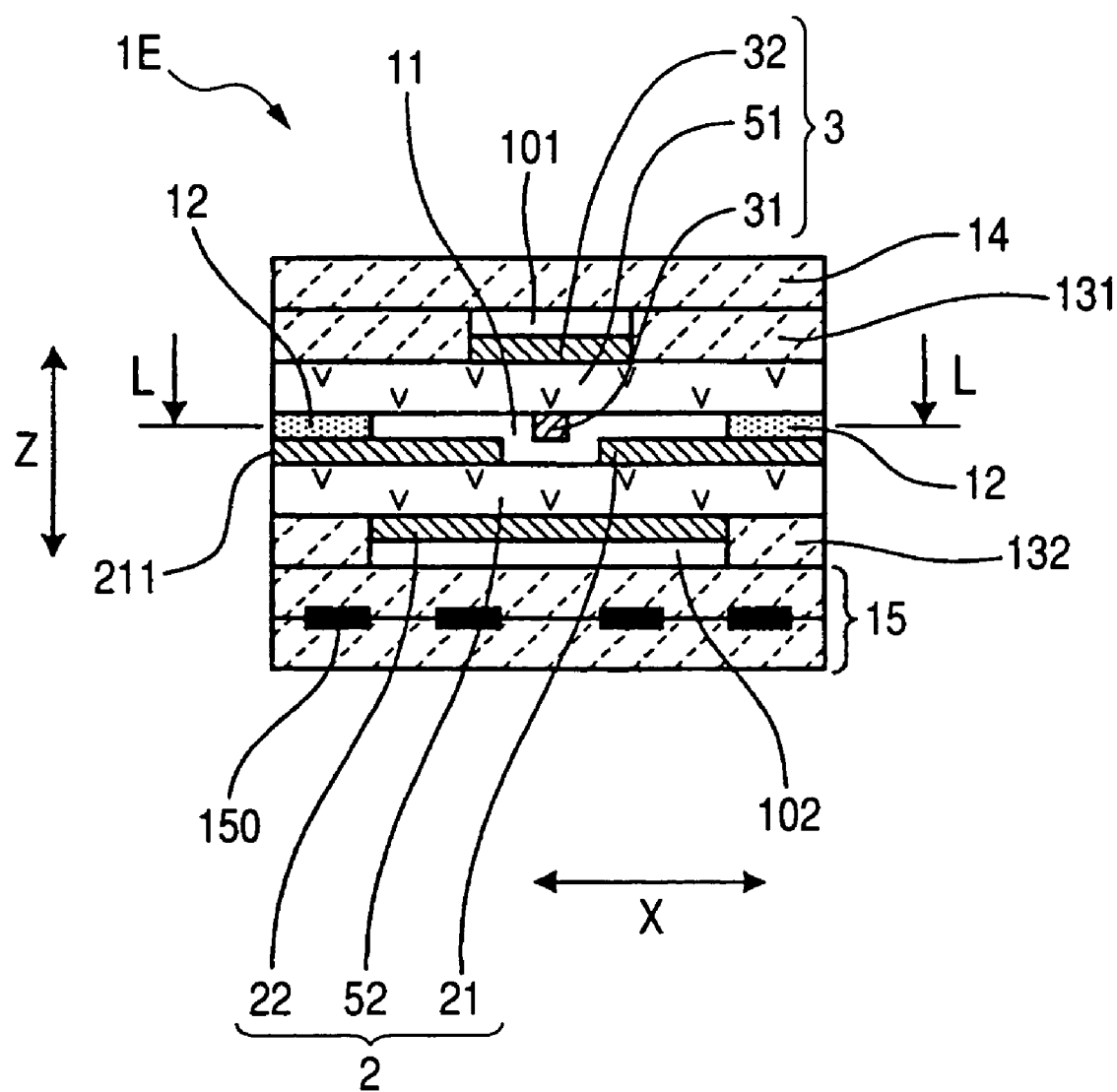
FIG. 18 is a cross sectional view of the gas sensing element taken on line K-K of FIG. 17.
Figure 19:
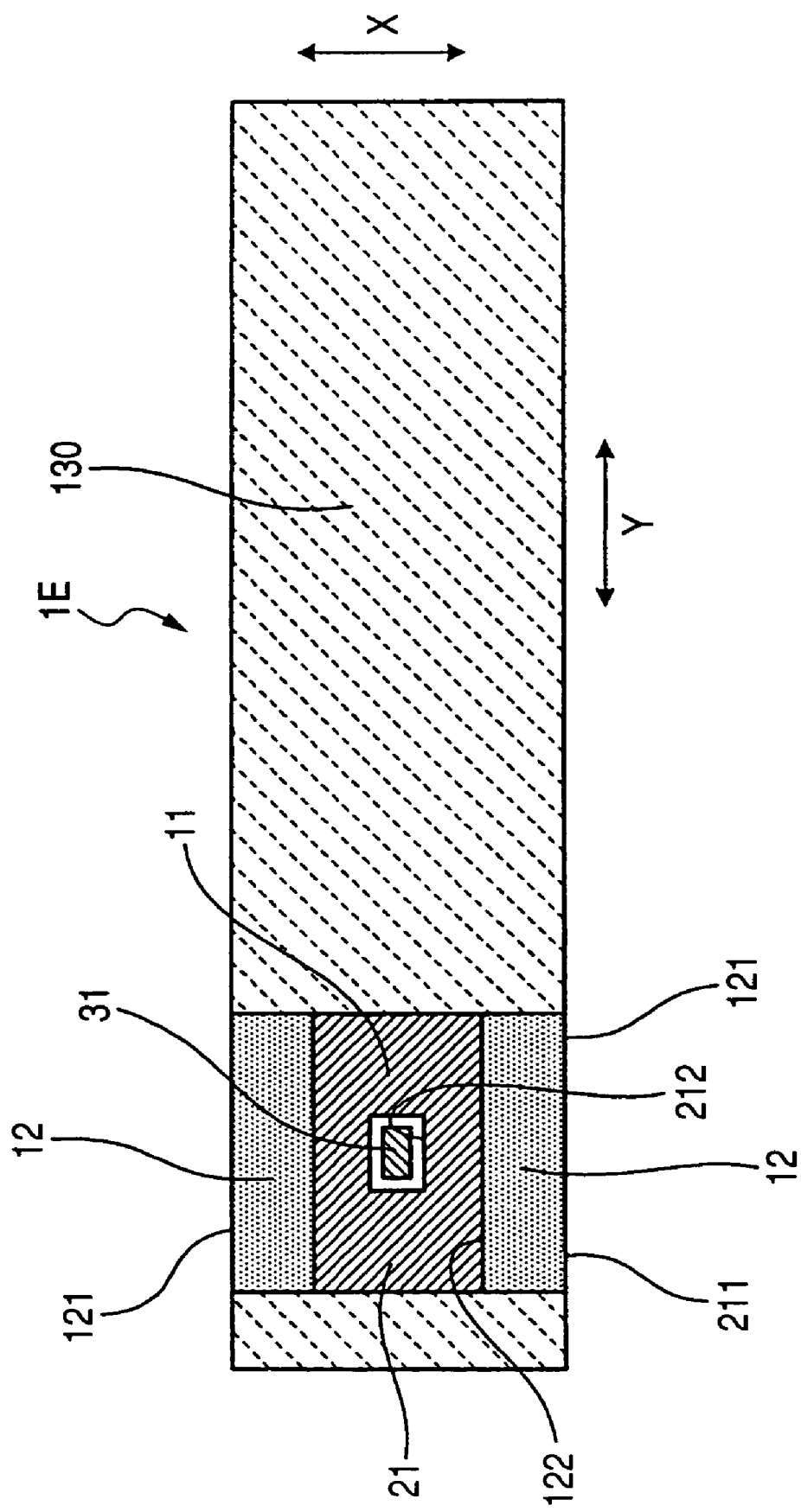
FIG. 19 is a cross sectional view of the gas sensing element taken on line L-L of FIGS. 17 and 18.

A gas sensing element 1E of a sixth embodiment will be described below in detail with reference to FIGS. 17 to 19 with like component parts bearing the same reference numerals as those of the gas sensing elements 1 to 1D of the first to fifth embodiments mentioned above.

The gas sensing element 1E of the sixth embodiment differs from the gas sensing elements 1 to 1D of the first to fifth embodiments in the absence of the monitor cell 4.

With such a structure, the oxygen pump cell 2 serves to adequately discharge oxygen from the measuring gas chamber 11 for decreasing the oxygen concentration to the extent in that the sensor cell 3 has no adverse affect in detecting the specified gas concentration (NOx concentration).

The gas sensing element 1E of the present embodiment has the same other structure as that of the gas sensing element 1 of the first embodiment With the present embodiment, the gas sensing element 1E can be easily manufactured in a simplified structure at low cost.

The gas sensing element 1E of the present modification performs the same operation as that of the gas sensing element 1 of the first embodiment and, hence, detailed description of the same is herein omitted.

Seventh Embodiment

Figure 20:
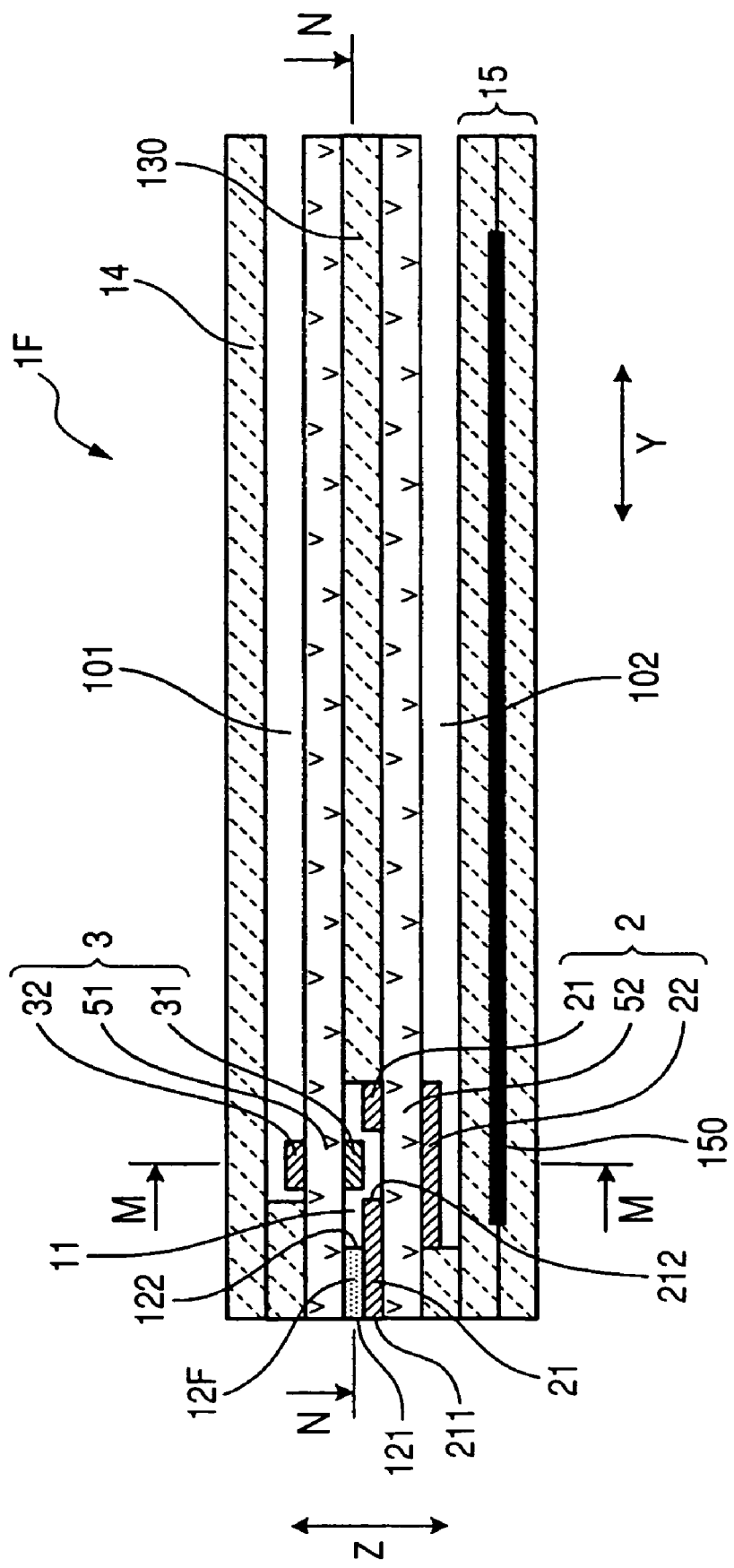
FIG. 20 is a view showing a gas sensing element of a seventh embodiment according to the present invention in cross section taken on a plane parallel to the longitudinal direction Y and the stack direction Z.

A gas sensing element 1F of a seventh embodiment will be described below in detail with reference to FIGS. 20 to 22 with like component parts bearing the same reference numerals as those of the gas sensing element 1 of the first embodiment mentioned above.

The gas sensing element 1F of the seventh embodiment differs from the gas sensing elements 1 of the first embodiment in that the gas sensing element 1F has a distal end formed with a diffusion resistance portion 12F.

Figure 21:
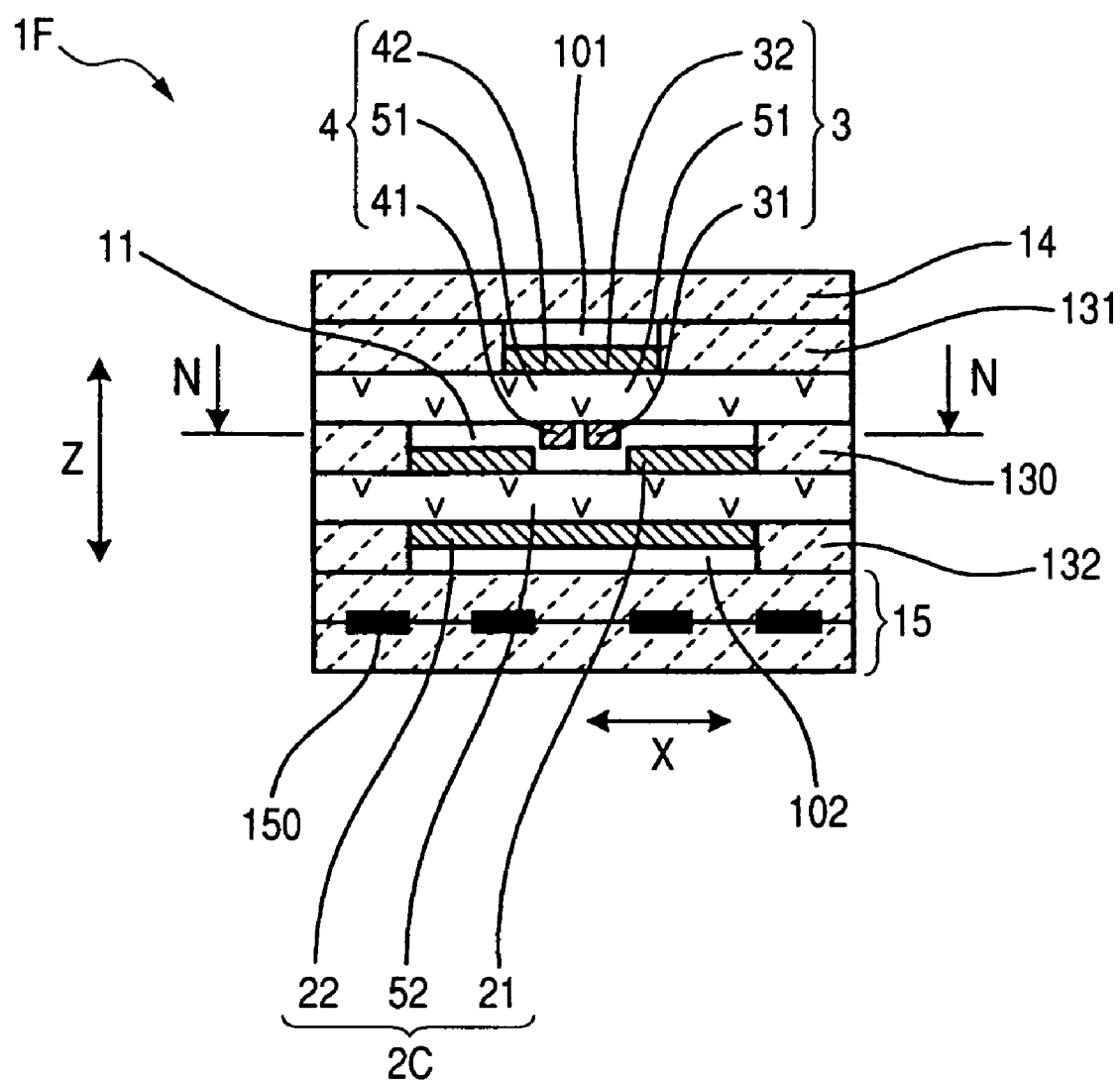
FIG. 21 is a cross sectional view of the gas sensing element taken on line M-M of FIG. 20.
Figure 22:
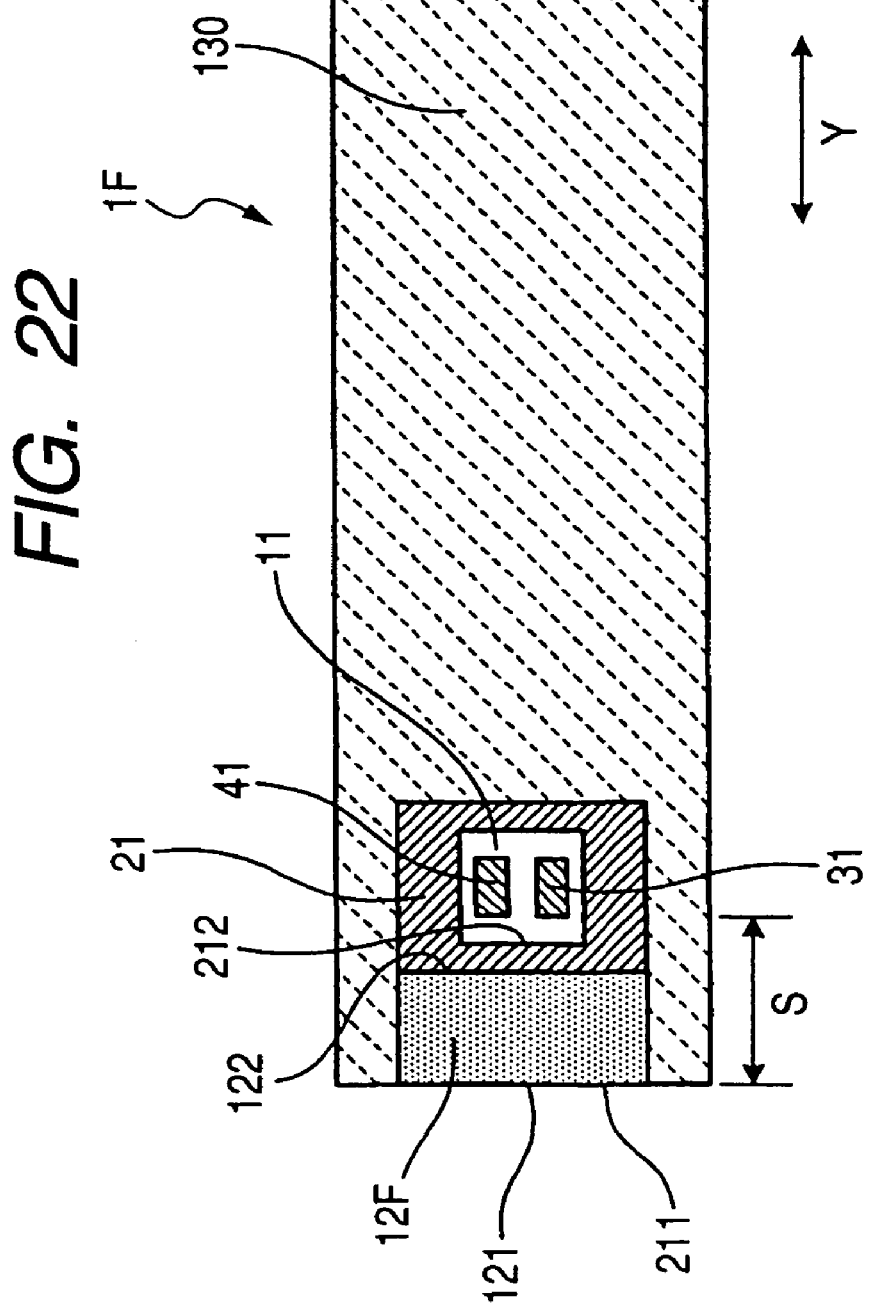
FIG. 22 is a cross sectional view of the gas sensing element taken on line N-N of FIGS. 20 and 21.

As will be apparent from FIGS. 21 and 22, further, the measuring electrode 31 of the sensor cell 3 and the inner monitor electrode 41 of the oxygen monitor cell 4 are formed on the first solid electrolyte body 51 to be spaced apart from each other in the widthwise direction X in parallel to each other.

The gas sensing element 1E of the present embodiment has the same other structure as that of the gas sensing element 1 of the first embodiment.

In normal practice, the sensor cell 3 is provided on the gas sensing element 1F in an area close proximity to the distal end thereof. Therefore, providing the diffusion resistance portions 12F on the distal end of the gas sensing element 1F along the longitudinal direction Y thereof makes it possible to adequately minimize the distance S between the external end wall of the diffusion resistance portions 12F, i.e., the inlet port for measuring gasses, and the measuring electrode 31.

As set forth above, further, locating the measuring electrode 31 and the inner monitor electrode 41 in the areas placed along the widthwise direction X in parallel to each other allows the measuring electrode 31 and the inner monitor electrode 41 to be spaced from the external end wall 12 of the diffusion resistance portions 12F by an equal distance. Thus, the oxygen concentration, detected with the oxygen monitor cell 4, and the oxygen concentration in measuring gases actually held in the measuring electrodes 31 can be equal to each other. This results in a capability of detecting the specified gas concentration (NOx concentration) of measuring gases with improved precision.

The gas sensing element 1F of the present embodiment has the same other structure as that of the gas sensing element 1 of the first embodiment.

Eighth Embodiment

Figure 23:
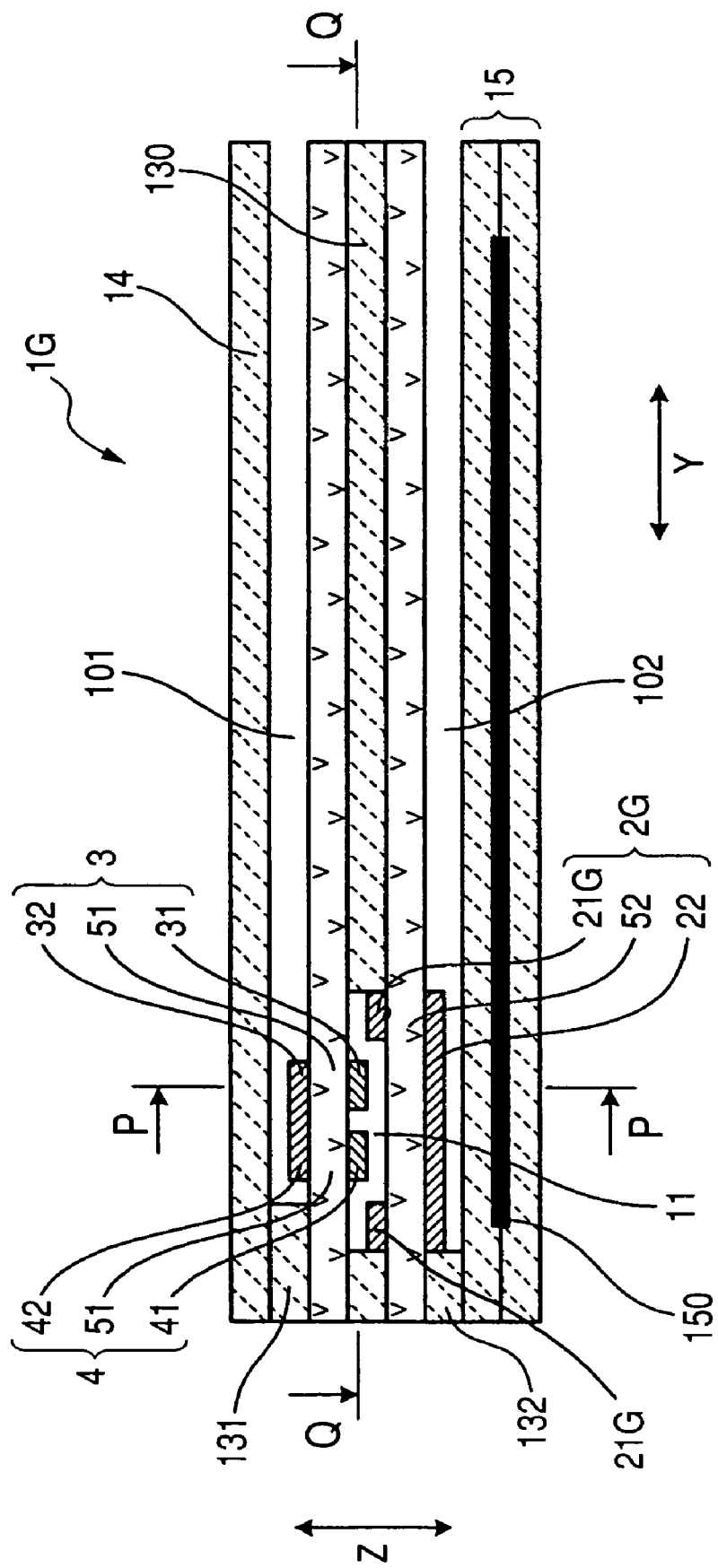
FIG. 23 is a view showing a gas sensing element of an eighth embodiment according to the present invention in cross section taken on a plane parallel to the longitudinal direction Y and the stack direction Z.
Figure 24:
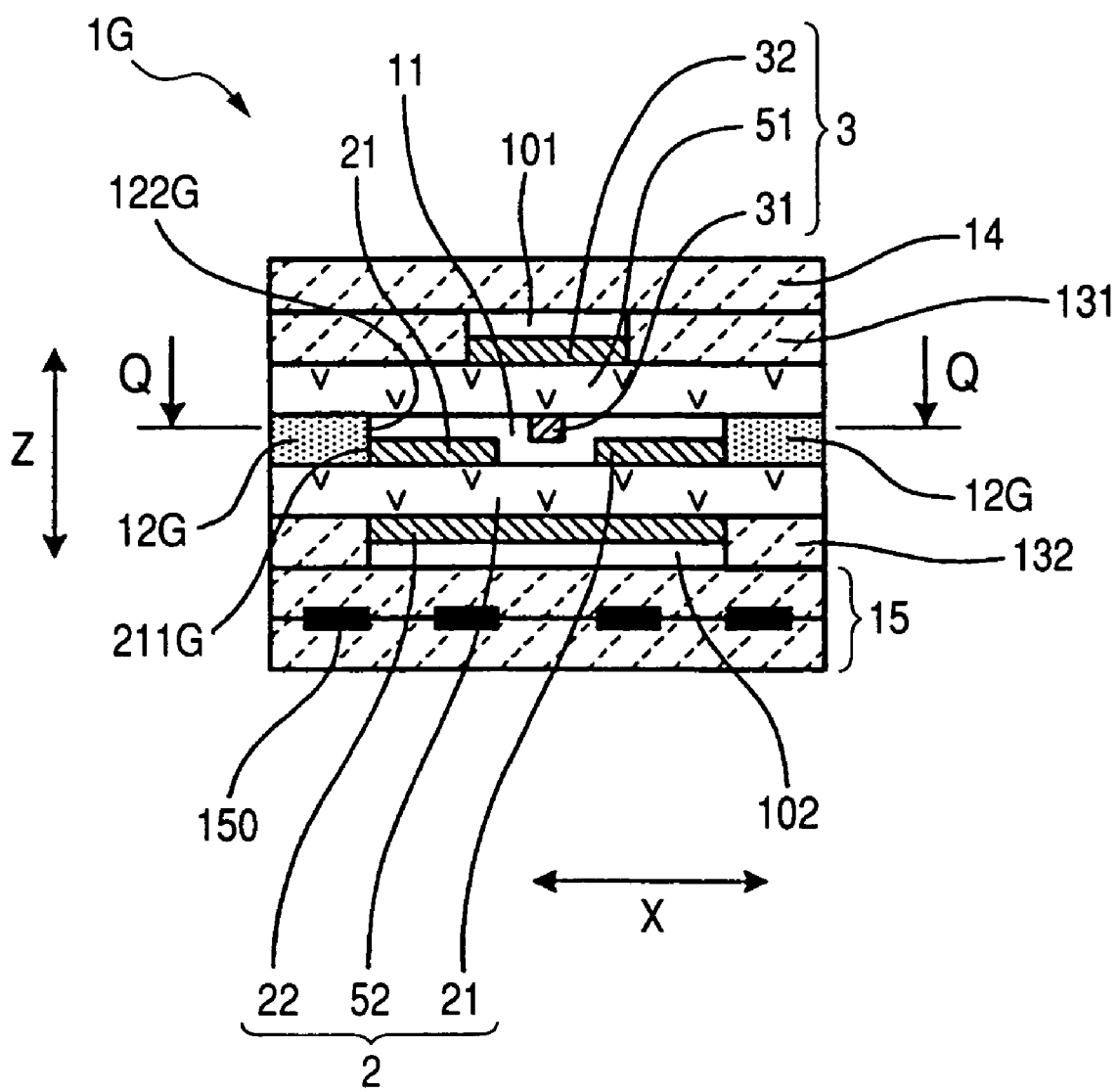
FIG. 24 is a cross sectional view of the gas sensing element taken on line P-P of FIG. 23.
Figure 25:
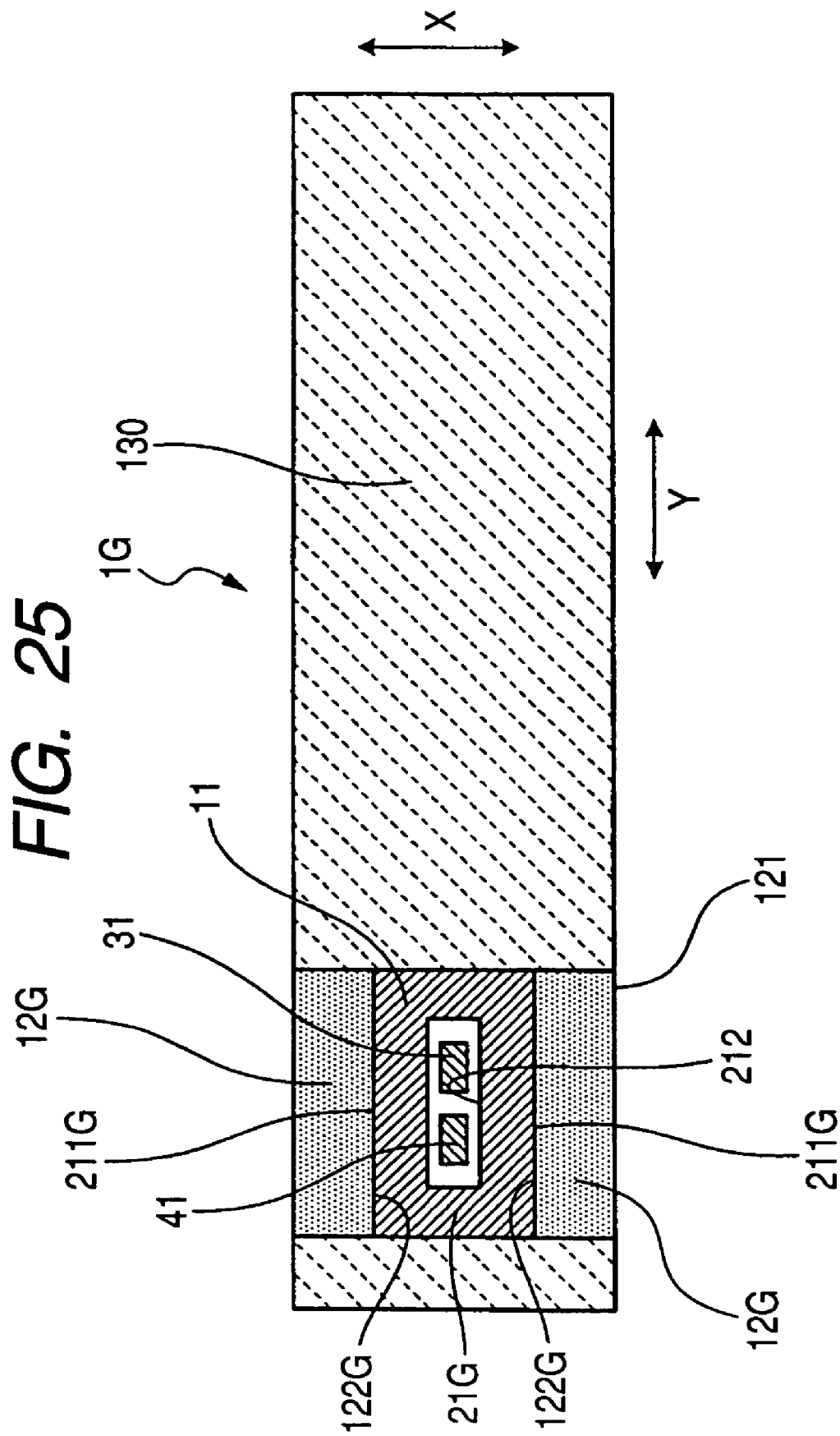
FIG. 25 is a cross sectional view of the gas sensing element taken on line Q-Q of FIGS. 23 and 24.
Figure 26:
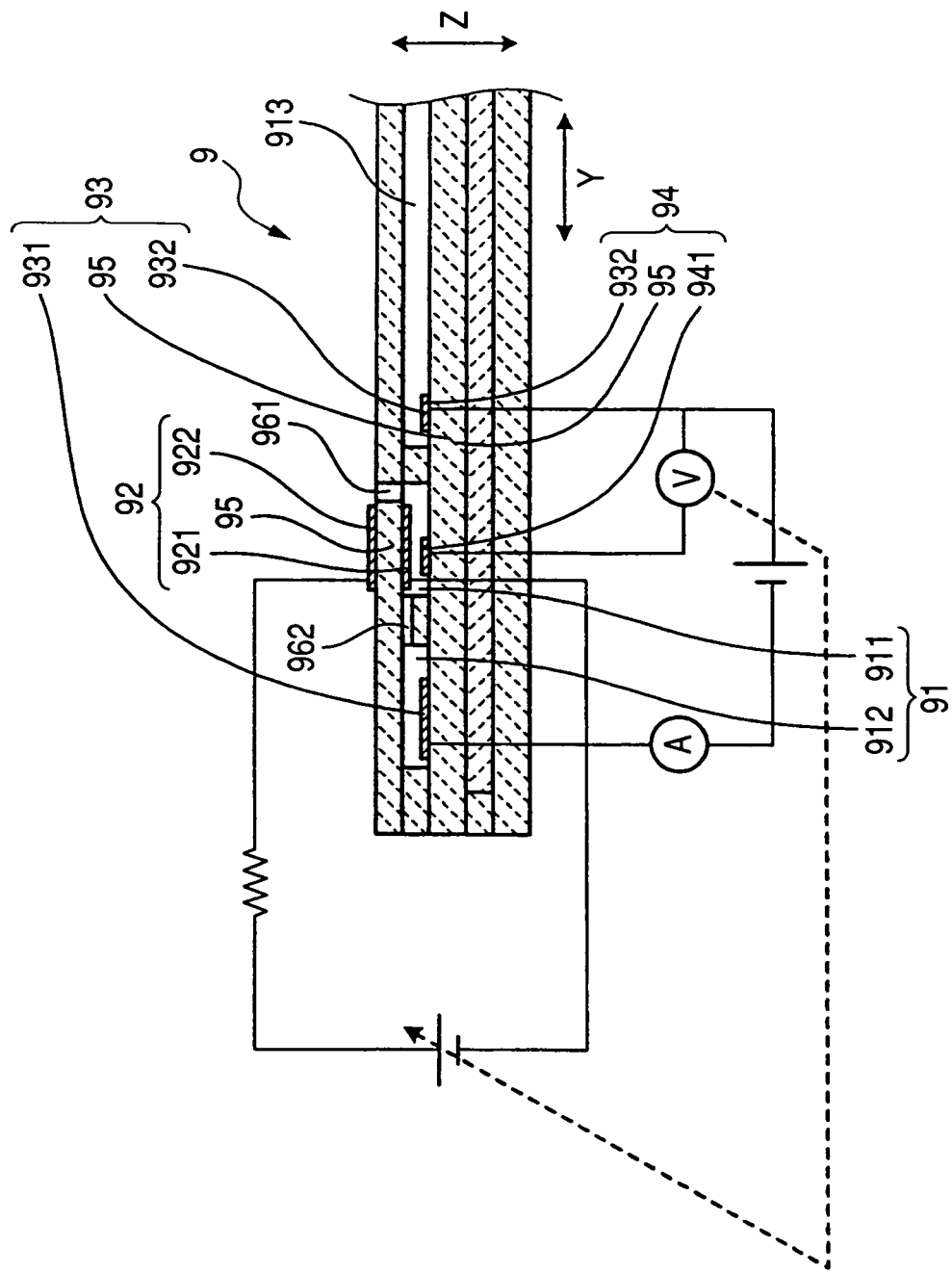
FIG. 26 is a view showing a gas sensing element of the related art in cross section taken on a plane parallel to the longitudinal direction Y and the stack direction Z.

A gas sensing element 1G of an eighth embodiment will be described below in detail with reference to FIGS. 23 to 25 with like component parts bearing the same reference numerals as those of the gas sensing element 1 of the first embodiment mentioned above.

The gas sensing element 1G of the present embodiment differs from the gas sensing elements 1 of the first embodiment in that an oxygen pump cell 2G includes an inner pump electrode 21G placed in an area inward of diffusion resistance portions 12G.

That is, the diffusion resistance portions 12G and the inner pump electrodes 21G are not overlapped in the stack direction Z. In addition, inner end walls 122G of the diffusion resistance portions 12G and an external end wall 211G of the inner pump electrode 21G are held in abutting contact with each other in the widthwise direction X.

The gas sensing element 1F of the present embodiment has the same other structure as that of the gas sensing element 1 of the first embodiment.

With the gas sensing element 1G of the present embodiment, measuring gases, reliably passed across the diffusion resistance portions 12G, can be brought into contact with the inner pump electrode 21G, thereby enabling the oxygen pump cell 2G to achieve a control of oxygen pumping capacity in a further reliable manner.

Thus, it becomes possible to obtain the gas sensing element 1G with excellent measuring precision.

The gas sensing element 1G of the present modification performs the same operation as that of the gas sensing element 1 of the first embodiment and, hence, detailed description of the same is herein omitted.

While the specific embodiments of the present invention have been described in detail, it will be appreciated by those skilled in the art that various modifications and alternatives to those details could be developed in light of the overall teachings of the disclosure. Accordingly, the particular arrangements disclosed are meant to be illustrative only and not limited to the scope of the present invention, which is to be given the full breadth of the following claims and all equivalents thereof.

What is claimed is:

1. A gas sensing element comprising:
   first and second solid electrolyte bodies extending in a longitudinal direction and stacked on each other in a stack direction with a space therebetween for defining a measuring gas chamber;
   a diffusion resistance portion placed adjacent to the measuring gas chamber to admit measuring gases thereto under given diffusion resistance;
   a sensor cell mounted on the first solid electrolyte body for detecting a specified gas concentration of measuring gases admitted to the measuring gas chamber;
   an oxygen pump cell mounted on the second solid electrolyte body for adjusting an oxygen concentration in the measuring gas chamber;
   the sensor cell including a measuring electrode, formed on a surface of the first solid electrolyte body facing the measuring gas chamber, and a reference electrode formed on the other surface of the first solid electrolyte body in pair with the measuring electrode;
   the oxygen pump cell including an inner pump electrode, formed on a surface of the second solid electrolyte body facing the measuring gas chamber, and an outer pump electrode formed on the other surface of the second solid electrolyte body in pair with the inner pump electrode;
   the diffusion resistance portion and the inner pump electrode being placed adjacent to each other in the stack direction; and
   the diffusion resistance portion extending from the measuring gas chamber in a plane perpendicular to the stack direction from a position inward of external end walls of the inner pump electrode terminating at the external end walls of the inner pump electrode;
   wherein the measuring electrode is located in the measuring gas chamber at an area inside of the inner pump electrode.

2. The gas sensing element according to claim 1, wherein:
   the diffusion resistance portion extends in a direction perpendicular to the longitudinal direction to the external end walls of the inner pump electrode.

3. The gas sensing element according to claim 1, wherein:
   the inner pump electrode and the measuring electrode are formed in areas juxtaposed along the longitudinal direction thereof, and the measuring electrode is spaced from an inner end wall of the inner pump electrode.

4. The gas sensing element according to claim 1, further comprising:
   an oxygen monitor cell mounted on the first solid electrolyte body for measuring an oxygen concentration in the measuring gas chamber; and
   the oxygen monitor cell including an inner monitor electrode, formed on the surface of the first solid electrolyte body facing the measuring gas chamber, and an outer monitor electrode formed on the other surface of the first solid electrolyte body in a pair with the inner monitor electrode;
   wherein the inner monitor electrode is located in an area inside the inner pump electrode.

5. The gas sensing element according to claim 4, wherein:
   the inner monitor electrode is spaced from an inner end wall of the inner pump electrode.

6. The gas sensing element according to claim 4, further comprising:
   a power supply for applying a voltage to the oxygen pump cell; and
   a pump circuit for regulating the voltage applied to the oxygen pump cell based on a detection signal on an oxygen concentration detected with the oxygen monitor cell.

7. The gas sensing element according to claim 4, further comprising:
   a first power supply for applying a given voltage across the measuring electrode and the reference electrode to allow an electric current to flow therebetween depending on the specified gas concentration and the oxygen concentration of the measuring gases; and
   a second power supply for applying a given voltage across the inner monitor electrode and the outer monitor electrode to allow an electric current to flow therebetween depending on the oxygen concentration of the measuring gases;
   wherein the specified gas concentration is detected based on a difference between a current value flowing through the sensor cell and a current value flowing through the oxygen monitor cell.

8. The gas sensing element according to claim 1, wherein:
   the diffusion resistance portion has at least a part composed of porous body.

9. The gas sensing element according to claim 1, wherein:
   the diffusion resistance portion is located between the measuring electrode and the inner pump electrode to act as diffusion resistance for the measuring gases.

10. The gas sensing element according to claim 1, wherein: an external end wall of the diffusion resistance portion and the measuring electrode are spaced by a distance of 1 to 3 mm.

11. The gas sensing element according to claim 1, wherein: the specified gas concentration includes nitrogen oxide concentration.

12. The gas sensing element according to claim 1, further comprising:
a diffusion resistance layer disposed between the inner pump electrode and the measuring electrode to provide diffusion resistance to the measuring gases acting on the measuring electrode.

13. The gas sensing element according to claim 1, wherein: the diffusion resistance portion has a slit formed in a minimized clearance to provide a given diffusion resistance.

14. The gas sensing element according to claim 1, wherein: the diffusion resistance portion is provided in a whole area of the measuring gas chamber so as to cover the inner monitor electrode and the measuring electrode.

15. The gas sensing element according to claim 1, further comprising:
a spacer disposed between the first and second solid electrolyte bodies formed with a restricted portion;
the measuring gas chamber includes first and second measuring gas chamber portions communicating with each other via the restricted portion; and
wherein the inner pump electrode is exposed to the second measuring gas chamber portion whereas the measuring electrode is exposed to the first measuring gas chamber portion.

16. The gas sensing element according to claim 1, wherein:
a first cell includes a reference electrode formed on the one surface of the first solid electrolyte body facing the reference gas compartment and a measuring electrode formed on the other surface of the first solid electrolyte body facing the measuring gas chamber; and
a second cell includes an inner pump electrode formed on the second solid electrolyte body on the one surface thereof facing the measuring gas chamber and an outer pump electrode formed on the other surface of the second solid electrolyte body facing the reference gas compartment;
wherein the measuring electrode is spaced from the inner pump electrode of the second cell.

17. The gas sensing element according to claim 1, wherein:
a first cell includes a reference electrode formed on the one surface of the first solid electrolyte body facing the reference gas compartment and a measuring electrode formed on the other surface of the first solid electrolyte body facing the measuring gas chamber;
a second cell includes a reference electrode formed on the one surface of the second solid electrolyte body facing the reference gas compartment and an inner pump electrode formed on the other surface of the second solid electrolyte body facing the measuring gas chamber; and
the gas sensing element further includes a third cell having an outer monitor electrode formed on the one surface of the first solid electrolyte body facing the reference gas compartment and an inner monitor electrode formed on the other surface of the first solid electrolyte body facing the measuring gas chamber;
wherein the diffusion resistance portion is formed on the other surface of the first solid electrolyte body at one distal end thereof; and
wherein the inner monitor electrode and the measuring electrode are formed on the other surface of the first solid electrolyte body in areas parallel to each other in a widthwise direction of the first solid electrolyte body.

18. The gas sensing element according to claim 1, wherein a first cell includes a reference electrode formed on one surface of the first solid electrolyte body facing the reference gas compartment and a measuring electrode formed on the other surface of the first solid electrolyte body facing the measuring gas chamber;
a second cell includes a reference electrode formed on one surface of the second solid electrolyte body facing the reference gas compartment and an inner pump electrode formed on the other surface of the second solid electrolyte body facing the measuring gas chamber; and
the gas sensing element further includes a third cell having an outer monitor electrode formed on the one surface of the first solid electrolyte body facing the reference gas compartment and an inner monitor electrode formed on the other surface of the first solid electrolyte body facing the measuring gas chamber;
wherein the diffusion resistance portion includes diffusion resistance layers disposed between the first and second solid electrolyte bodies on both sides thereof at distal end portions the first and second solid electrolyte bodies;
wherein the inner pump electrode is placed in an area inward of the diffusion resistance layers; and
wherein the inner monitor electrode and the measuring electrode are formed on the other surface of the first solid electrolyte body in areas parallel to each other in a longitudinal direction of the first solid electrolyte body.

19. A gas sensing element comprising:
first and second solid electrolyte bodies extending in a longitudinal direction and stacked on each other in a stacked direction;
a measuring gas chamber formed between the first and second solid electrolyte bodies;
a reference gas chamber defined on one surface of the first solid electrolyte body;
a sensor cell mounted on the first solid electrolyte body for detecting a specified gas concentration of measuring gases admitted to the measuring gas chamber;
an oxygen pump cell mounted on the second solid electrolyte body for adjusting an oxygen concentration in the measuring gas chamber;
the sensor cell including a measuring electrode, formed on the other surface of the first solid electrolyte body facing the measuring gas chamber, and a reference electrode formed on one surface of the first solid electrolyte body in pair with the measuring electrode to be exposed to the reference gas chamber;
the oxygen pump cell including an inner pump electrode disposed in the measuring gas chamber, and an outer pump electrode formed on the other surface of the second solid electrolyte body in pair with the inner pump electrode; and
a diffusion resistance portion, placed between the first and second solid electrolyte bodies exposed to the measuring gas chamber, and which extends in parallel to the inner pump electrode in close proximity thereto for admitting measuring gases to the measuring gas chamber under given diffusion resistance;
the diffusion resistance portion terminates at the external end walls of the inner pump electrode;
wherein the measuring electrode is located in the measuring gas chamber at an area inside of the inner pump electrode.

* * * * *